(12) United States Patent
Kuimelis et al.

(10) Patent No.: US 8,835,125 B2
(45) Date of Patent: Sep. 16, 2014

(54) METHODS AND COMPOSITIONS FOR SELECTIVE LABELING OF DIFFERENT BIOTINYLATED TARGETS WITHIN MULTICOLOR OR MULTILABEL ASSAYS

(75) Inventors: Robert G. Kuimelis, Palo Alto, CA (US); Glenn H. McGall, Palo Alto, CA (US); Stephen P. A. Fodor, Palo Alto, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 13/329,175

(22) Filed: Dec. 16, 2011

(65) Prior Publication Data

US 2012/0226027 A1 Sep. 6, 2012

Related U.S. Application Data

(60) Provisional application No. 61/424,301, filed on Mar. 2, 2011.

(51) Int. Cl.
*G01N 1/00* (2006.01)
*G01N 33/00* (2006.01)
*G01N 33/53* (2006.01)
*C12Q 1/00* (2006.01)
*C12N 9/00* (2006.01)

(52) U.S. Cl.
USPC .............. 435/7.5; 435/4; 435/7.1; 435/7.6; 435/7.72; 435/7.9; 435/7.93; 435/7.94; 435/7.95; 435/183; 435/188; 436/8; 436/15; 436/17; 436/175; 436/177; 436/501; 436/544

(58) Field of Classification Search
None
See application file for complete search history.

(56) References Cited

U.S. PATENT DOCUMENTS

2010/0099159 A1 * 4/2010 Deiters .................. 435/173.1

FOREIGN PATENT DOCUMENTS

WO WO 2006/071247 * 7/2006 .............. C12Q 1/68

OTHER PUBLICATIONS

Hirsch et al., (Anal. Biochem. 2002. vol. 308, pp. 343-357).*

* cited by examiner

*Primary Examiner* — Ja'Na Hines
(74) *Attorney, Agent, or Firm* — Banner & Witcoff, Ltd.

(57) ABSTRACT

Disclosed are compositions and methods for the labeling of two or more targets with different labels. Specifically, disclosed are compositions for biotin and the protection of biotin within multilabel assays which employ the biotin-biotin binding protein binding relationship for each distinct label in relation to targets such as nucleic acids, polypeptides, antibodies or cells. These multilabel assays are enabled through the use of biotin with desthiobiotin, orthogonal protecting schemes for biotin, or a combination of the approaches.

15 Claims, 18 Drawing Sheets

X=286, Y=60: intensity 5964
X=287, Y=60: intensity 5680
X=288, Y=60: intensity 4781

X=286, Y=60: intensity 58
X=287, Y=60: intensity 58
X=288, Y=60: intensity 58

Signal intensity: 1668
Background: 137

Signal intensity: 88
Background: 57

Signal intensity: 1743
Background: 130

METHODS AND COMPOSITIONS FOR SELECTIVE LABELING OF DIFFERENT BIOTINYLATED TARGETS WITHIN MULTICOLOR OR MULTILABEL ASSAYS

RELATED APPLICATIONS

This application claims priority to U.S. Provisional Patent Application No. 61/424,301, filed Mar. 2, 2011, which is incorporated herein by reference in its entirety for all purposes.

FIELD OF THE INVENTION

The presently disclosed compositions and methods provided herein are for the use of biotin and variants thereof within labeling and detection schemes employing the associated use of biotin binding proteins. More specifically, disclosed herein are compositions and methods with which multi-color labeling and detection schemes employ one or more variants of biotin and/or one or more forms of protected biotin.

BACKGROUND OF THE INVENTION

Biotin has long been employed within the life sciences for a variety of applications because of several characteristics, including its small size, relatively easy ability to incorporated into a variety of materials and substances (i.e., biotinylation), and its high affinity for certain proteins (e.g., biotin binding proteins such as avidin, streptavidin and related recombinations, analogs and derivatives). The small size of biotin enhances its ability to be incorporated or otherwise label a material or substance without affecting its biological activity, interaction with other molecules, etc. Furthermore, through the labeling of biotin binding proteins with various labels, the high binding affinity for these proteins with biotin thus facilitates labeling of targets of interests within assays of many different types. Many assays in the life sciences utilize two or distinct labels (e.g., two types of fluorophores with distinct emission characteristics), and of these assays, a great number utilize biotin and a biotin binding protein conjugated with a label as part of the labeling scheme. However, the use of different binding pairs, often with inferior binding characteristics, within these labeling schemes to provide additional label types can lead to undesirable labeling results and/or increase the difficulty of obtaining accurate results. Thus, there remains a need for the facilitation of multi-color labeling approaches where each of the binding pairs for the labels involved employ a biotin-biotin binding protein approach.

SUMMARY OF THE INVENTION

Disclosed herein are compositions and methods for labeling a plurality of targets with a plurality of labels. Specifically, compositions and methods are provided for utilizing the high binding affinity of biotin and its related derivatives and analogs, such as desthiobiotin, with a wide range of suitable biotin binding proteins, such as avidin, streptavidin and recombinant versions thereof. Two or more targets are each biotinylated with a different biotin molecule, whether the biotin molecule is a different type of biotin (e.g., desthiobiotin), or whether the biotin molecule is protected with a suitable protecting group (e.g., photolabile, acid-labile, and base-labile protecting groups). This differentiation of the biotins associated with the various targets at issue allows selective binding with different biotin binding proteins, where each different biotin binding protein is directly or indirectly associated with a distinct label. This allows the various targets, such as nucleic acids, polypeptides, antibodies or cells, to be differentially labeled even though each of the binding pairs employs the biotin-biotin binding protein relationship and its well known characteristics and advantages, such as high binding affinities and the small size of biotin.

Furthermore, disclosed herein are compositions and methods for expanding these labeling schemes from the labeling of two different targets with two different labels to 4-label assays or greater. For example, disclosed herein are compositions and methods for 2, 3, 4, 5, 6, 7, 8, 9, 10 or more distinct labels to be selected employed within an assay. Labels may be any suitable label for the assay at issue, including fluorescent, luminescent, chemiluminescent, light-scattering, and colorimetric labels. Moreover, the utilization of biotin and biotin derivatives and analogs can be combined with orthogonal protecting schemes for biotin to more easily enable 4, 6, 8, etc. label assays. Particularly suitable protecting groups include DMT and NPOM, especially NPOM which is linked with the biotin molecule at issue through an ether linkage, but any suitable photolabile, acid-labile, base-labile or other protecting group (such as those removed by hydrogenolysis) which is appropriate for the scheme at issue may be employed.

DETAILED DESCRIPTION

Figure 1A:
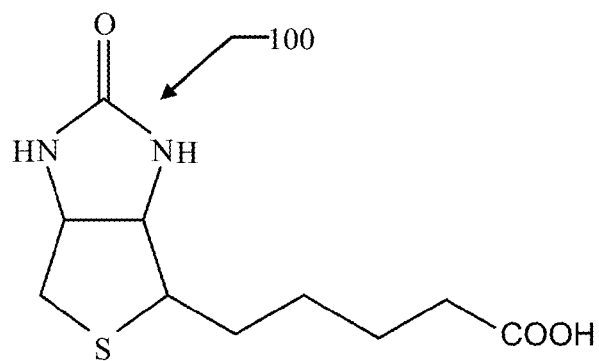
FIG. 1(A) illustrates a structural depiction of biotin.

The present invention has many preferred embodiments and relies on many patents, patent applications and other references for details known to those of ordinary skill in the art to which the invention pertains. Therefore, when a reference, such as a patent, patent application, and other publication is cited or otherwise mentioned within any section of this specification, it should be understood that the reference is incorporated by reference in its entirety for all purposes as well as for the proposition that is recited and/or the precise context in which the reference is cited.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques may include polymer array synthesis, hybridization, ligation, and detection of hybridization using a label. Specific illustrations of suitable techniques can be had by reference to the embodiments described herein. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, Biochemistry, $4^{th}$ Ed., W.H. Freeman & Company (1995), Gait, "Oligonucleotide Synthesis: A Practical Approach," IRL Press, London (1984), Nelson and Cox, Lehninger, Principles of Biochemistry $3^{rd}$ Ed., W.H. Freeman Pub., New York, N.Y. (2000), and Berg et al., Biochemistry, $5^{th}$ Ed., W.H. Freeman Pub., New York, N.Y. (2002), all of which are herein expressly incorporated by reference in their entirety for all purposes.

Embodiments of the present invention may utilize enzymatic activities. A variety of enzymes are well known, have been characterized and many are commercially available from one or more supplier. For a review of enzyme activities commonly used in molecular biology see, for example, Rittie and Perbal, J. Cell Commun. Signal., 2: 25-45 (2008). Exemplary enzymes include DNA dependent DNA polymerases (such as those shown in Table 1 of Rittie and Perbal), RNA dependent DNA polymerase (see Table 2 of Rittie and Perbal), RNA polymerases, ligases (see Table 3 of Rittie and Perbal), enzymes for phosphate transfer and removal (see Table 4 of Rittie and Perbal), nucleases (see Table 5 of Rittie and Perbal), and methylases.

Nucleic acid arrays may be employed in various embodiments, with commercially available arrays including GeneChip® and Axiom® arrays from Affymetrix, Inc. (Santa Clara, Calif.), Infinium® and GoldenGate® arrays from Illumina, Inc. (San Diego, Calif.), NimbleGen® arrays from Roche NimbleGen, Inc. (Madison, Wis.), Agilent® arrays from Agilent Technologies, Inc. (Santa Clara, Calif.). Such arrays may be employed within, for example, molecular diagnostics, copy number analysis, genome-wide genotyping, drug metabolism analysis, molecular cytogenetics, resequencing analysis, targeted genotyping analysis, expression analysis, gene regulation analysis, miRNA analysis, whole-transcript expression analysis and profiling, and other uses known in the art. Various methods of gene expression monitoring and profiling are described in, for example, U.S. Pat. Nos. 5,800,992; 6,013,449; 6,020,135; 6,033,860; 6,040,138; 6,177,248 and 6,309,822. Genotyping methods are disclosed in, for instance, U.S. Pat. Nos. 5,856,092; 6,300,063; 5,858,659; 6,284,460; 6,361,947; 6,368,799; 6,333,179 and 6,872,529. Other uses of arrays are described in, for example, U.S. Pat. Nos. 5,871,928; 5,902,723; 6,045,996; 5,541,061 and 6,197,506. Methods and techniques applicable to polymer array synthesis have been described in the art, for example, in International Patent Publication Nos. WO 99/36760; WO 00/58516 and WO 01/58593; and U.S. Pat. Nos. 5,143,854; 5,242,974; 5,252,743; 5,324,633; 5,384,261; 5,405,783; 5,424,186; 5,451,683; 5,482,867; 5,491,074; 5,527,681; 5,550,215; 5,571,639; 5,578,832; 5,593,839; 5,599,695; 5,624,711; 5,631,734; 5,795,716; 5,831,070; 5,837,832; 5,856,101; 5,858,659; 5,936,324; 5,968,740; 5,974,164; 5,981,185; 5,981,956; 6,025,601; 6,033,860; 6,040,193; 6,090,555; 6,136,269; 6,269,846; and 6,428,752, all of which are incorporated herein by reference in their entireties for all purposes.

The synthesis of oligonucleotides on the surface of a substrate may be carried out using light directed methods as described in., e.g., U.S. Pat. Nos. 5,143,854 and 5,384,261 and PCT Publication No. WO 92/10092, or mechanical synthesis methods as described in U.S. Pat. Nos. 5,384,261, 6,040,193 and PCT Publication No. 93/09668, each of which is incorporated herein by reference. In particular, these light-directed or photolithographic synthesis methods involve a photolysis step and a chemistry step. The substrate surface, prepared as described herein, comprises functional groups on its surface. These functional groups are protected by photolabile protecting groups. During the photolysis step, portions of the surface of the substrate are exposed to light or other activators to activate the functional groups within those portions, e.g., to remove photolabile groups. The substrate is then subjected to a chemistry step in which chemical monomers that are photoprotected at least one functional group are then contacted with the surface of the substrate. These monomers bind to the activated portion of the substrate through an unprotected functional group. Repetitions of the activation and coupling steps may be employed in sets of preselected regions, which may overlap, at least in part, with the first set of preselected regions, to create an array of polymers with different sequences within the regions of the substrate.

Preparation methods for samples of nucleic acids are well known in the art. Certain methods may implement amplification by a variety of mechanisms, some of which may employ PCR. (See, e.g., PCR Technology: Principles and Applications for DNA Amplification, Ed. H. A. Erlich, Freeman Press, NY, N.Y., 1992; PCR Protocols: A Guide to Methods and Applications, Eds. Innis, et al., Academic Press, San Diego, Calif., 1990; Mattila et al., Nucleic Acids Res., 19: 4967 (1991); Eckert et al., PCR Methods and Applications, 1:17 (1991); PCR, Eds. McPherson et al., IRL Press, Oxford (1991); and U.S. Pat. Nos. 4,683,202; 4,683,195; 4,800,159; 4,965,188 and 5,333,675, each of which is incorporated herein by reference in their entireties for all purposes. Isothermal amplification methods have also been developed. One of them is known as Strand Displacement Amplification (SDA). SDA combines the ability of a restriction endonuclease to nick the unmodified strand of its target DNA and the action of an exonuclease-deficient DNA polymerase to extend the 3' end at the nick and displace the downstream DNA strand. The displaced strand serves as a template for an antisense reaction and vice versa, resulting in exponential amplification of the target DNA (See, e.g., U.S. Pat. Nos. 5,455,166 and 5,470,723). Another isothermal amplification system, Transcription-Mediated Amplification (TMA), utilizes the function of an RNA polymerase to make RNA from a promoter engineered in the primer region, and a reverse transcriptase, to produce DNA from the RNA templates. This RNA amplification technology has been further improved by introducing a third enzymatic activity, RNase H, to remove the RNA from cDNA without the heat-denaturing step. Thus the thermo-cycling step has been eliminated, generating an isothermal amplification method named Self-Sustained Sequence Replication (3SR) (See, e.g., Guatelli et al., Proc. Natl. Acad. Sci. USA 87:1874-1878 (1990)). The starting material for TMA and 3SR is RNA molecules. Many other amplification techniques, and sample preparation methods in general, are known to those of skill in the art.

Other suitable sample amplification methods include the ligase chain reaction (LCR) (see, e.g., Wu and Wallace, Genomics, 4: 560 (1989); Landegren et al., Science, 241: 1077 (1988); and Barringer et al., Gene, 89: 117 (1990)), transcription amplification (Kwoh et al., Proc. Natl. Acad. Sci. USA, 86: 1173 (1989) and WO 88/10315), self-sustained sequence replication (Guatelli et al., Proc. Nat. Acad. Sci. USA, 87: 1874 (1990) and WO 90/06995), selective amplification of target polynucleotide sequences (e.g., U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909 and 5,861,245) and nucleic acid based sequence amplification (NABSA). (See also, U.S. Pat. Nos. 5,409,818; 5,554,517; and 6,063,603, each of which is incorporated herein by reference). Other amplification methods that may be used are described in, for instance, U.S. Pat. Nos. 6,582,938; 5,242,794; 5,494,810 and 4,988,617, each of which is incorporated herein by reference. Additional methods of sample preparation and techniques for reducing the complexity of a nucleic sample are described in Dong et al., Genome Research, 11:1418 (2001), U.S. Pat. Nos. 6,361,947; 6,391,592; 6,632,611; 6,872,529 and 6,958,225.

Another amplification method, Rolling Circle Amplification (RCA), generates multiple copies of a sequence for the use in in vitro DNA amplification adapted from in vivo rolling circle DNA replication (See, e.g., Fire and Xu, Proc. Natl. Acad. Sci. USA 92:4641-4645 (1995); Lui, et al., J. Am. Chem. Soc. 118:1587-1594 (1996); Lizardi, et al., Nature Genetics 19: 225-232 (1998), U.S. Pat. Nos. 5,714,320 and 6,235,502). In this reaction, a DNA polymerase extends a primer on a circular template generating tandemly linked copies of the complementary sequence of the template. RCA has been further developed in a technique, named Multiple Displacement Amplification (MDA), which generates a highly uniform representation in whole genome amplification (See, e.g., Dean et. al., Proc. Natl. Acad. Sci. USA 99:5261-5266 (2002)).

Methods for conducting polynucleotide hybridization assays have been well developed in the art. Hybridization assay procedures and conditions will vary depending on the application and are selected in accordance with known general binding methods, including those referred to in Maniatis et al., Molecular Cloning: A Laboratory Manual, 2d Ed., Cold Spring Harbor, N.Y., (1989); Berger and Kimmel, Methods in Enzymology, Guide to Molecular Cloning Techniques, Vol. 152, Academic Press, Inc., San Diego, Calif. (1987); Young and Davism, Proc. Nat'l. Acad. Sci., 80: 1194 (1983). Methods and apparatus for performing repeated and controlled hybridization reactions have been described in, for example, U.S. Pat. Nos. 5,871,928; 5,874,219; 6,045,996; 6,386,749 and 6,391,623, each of which are incorporated herein by reference. The invention also contemplates signal detection of hybridization between ligands in certain embodiments. (See, e.g., U.S. Pat. Nos. 5,143,854; 5,578,832; 5,631,734; 5,834,758; 5,936,324; 5,981,956; 6,025,601; 6,141,096; 6,185,030; 6,201,639; 6,218,803 and 6,225,625, each of which is hereby incorporated by reference in its entirety for all purposes). Many other related techniques and developments thereof are also known in the art.

Described herein are various chemical structures for use within various embodiments. As described or depicted herein, an alkyl group refers to a straight or branched hydrocarbon chain containing the specified number of carbon atoms. If alkyl is used without reference to a number of carbon atoms, it is to be understood to refer to a $C_1$-$C_{10}$ alkyl. For example, $C_{1-10}$ alkyl refers to a straight or branched alkyl containing at least 1, and at most 10, carbon atoms. Examples of alkyls include, but are not limited to, methyl, ethyl, n-propyl, n-butyl, n-pentyl, isobutyl, isopropyl, t-butyl, hexyl, heptyl, octyl, nonyl and decyl.

Aryl refers to an aromatic monovalent carboxylic radical having a single ring (e.g., phenyl) or two condensed rings (e.g., naphthyl), which can optionally be mono-, di-, or tri-substituted, independently, with alkyl, lower-alkyl, cycloalkyl, ydroxylower-alkyl, aminoloweralkyl, hydroxyl, thiol, amino, halo, nitro, lower-alkylthio, lower-alkoxy, mono-lower-alkylamino, di-lower-alkylamino, acyl, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl. Cycloalkyl groups generally refer to a non-aromatic monocyclic hydrocarbon ring of 3 to 8 carbon atoms such as, for example, cyclopropyl, cyclobutyl, cyclopentyl, cyclohexyl or cycloheptyl.

Alternatively, two adjacent positions of the aromatic ring may be substituted with a methylenedioxy or ethylenedioxy group. Heteroaromatic refers to an aromatic monovalent mono- or poly-cyclic radical having at least one heteroatom within the ring, e.g., nitrogen, oxygen or sulfur, wherein the aromatic ring can optionally be mono-, di- or tri-substituted, independently, with alkyl, lower-alkyl, cycloalkyl, hydroxylower-alkyl, aminolower-alkyl, hydroxyl, thiol, amino, halo, nitro, lower-alkylthio, loweralkoxy, mono-lower-alkylamino, di-lower-alkylamino, acyl, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, loweralkylcarbamoyl, and di-lower-alkylcarbamoyl. For example, typical heteroaryl groups with one or more nitrogen atoms are tetrazoyl, pyridyl (e.g., 4-pyridyl, 3-pyridyl, 2-pyridyl), pyrrolyl (e.g., 2-pyrrolyl, 2-(N-alkyl)pyrrolyl), pyridazinyl, quinolyl (e.g. 2-quinolyl, 3-quinolyl etc.), imidazolyl, isoquinolyl, pyrazolyl, pyrazinyl, pyrimidinyl, pyridonyl or pyridazinonyl; typical oxygen heteroaryl radicals with an oxygen atom are 2-furyl, 3-furyl or benzofuranyl; typical sulfur heteroaryl radicals are thienyl, and benzothienyl; typical mixed heteroatom heteroaryl radicals are furazanyl and phenothiazinyl.

Substitution of chemical groups may, in certain circumstances, be optional, and thus optionally substituted refers to the presence or lack thereof of a substituent on the group being defined. When substitution is present the group may be mono-, di- or tri-substituted, independently, with alkyl, lower-alkyl, cycloalkyl, hydroxylower-alkyl, aminoloweralkyl, hydroxyl, thiol, amino, halo, nitro, lower-alkylthio, lower-alkoxy, mono-lower-alkylamino, di-lower-alkylamino, acyl, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl. Typically, electron-donating substituents such as alkyl, lower-alkyl, cycloalkyl, hydroxylower-alkyl, aminoloweralkyl, hydroxyl, thiol, amino, halo, lower-alkylthio, loweralkoxy, mono-lower-alkylamino and di-lower-alkylamino are often preferable.

Substituted alkyls generally refer to alkyl radicals wherein at least one hydrogen is replaced by one more substituents such as, but not limited to, hydroxy, alkoxy, aryl (for example, phenyl), heterocycle, halogen, trifluoromethyl, pentafluoroethyl, cyano, cyanomethyl, nitro, amino, amide (e.g., —C(O)NH—R where R is an alkyl such as methyl), amidine, amido (e.g., —NHC(O)—R where R is an alkyl such as methyl), carboxamide, carbamate, carbonate, ester, alkoxyester (e.g., —C(O)O—R where R is an alkyl such as methyl) and acyloxyester (e.g., —OC(O)—R where R is an alkyl such as methyl), or two hydrogens on a single carbon is replaced with oxygen to provide a carbonyl group. T Substituted cycloalkyls generally refer to a cycloalkyl group which further bears one or more substituents as set forth herein, such as, but not limited to, hydroxy, alkoxy, aryl (for example, phenyl), heterocycle, halogen, trifluoromethyl, pentafluoroethyl, cyano, cyanomethyl, nitro, amino, amide (e.g., —C(O)NH—R where R is an alkyl such as methyl), amidine, amido (e.g., —NHC(O)—R where R is an alkyl such as methyl), carboxamide, carbamate, carbonate, ester, alkoxyester (e.g., —C(O)O—R where R is an alkyl such as methyl) and acyloxyester (e.g., —OC(O)—R where R is an alkyl such as methyl), or two hydrogen atoms on a single carbon is replaced with oxygen to provide a carbonyl group.

The practice of embodiments of the present invention may also employ conventional software methods and systems. Computer software products utilized with embodiments of the present invention generally include computer readable medium having computer-executable instructions for performing various steps directly or indirectly associated with aspects of the present invention. Suitable computer readable medium include floppy disk, CD-ROM/DVD/DVD-ROM, hard-disk drive (e.g., utilized locally and/or over a network), flash memory, ROM/RAM, magnetic tapes and etc. The computer executable instructions may be written in a suitable computer language or combination of several languages. Basic computational biology methods are described in, e.g. Setubal and Meidanis et al., Introduction to Computational Biology Methods, PWS Publishing Company, Boston (1997), Salzberg, Searles, Kasif, (Ed.), Computational Methods in Molecular Biology, Elsevier, Amsterdam (1998), Rashidi and Buehler, Bioinformatics Basics: Application in Biological Science and Medicine, CRC Press, London (2000) and Ouelette and Bzevanis Bioinformatics: A Practical Guide for Analysis of Gene and Proteins, Wiley & Sons, Inc., $2^{nd}$ ed. (2001). Embodiments may also make use of various computer program products and software for a variety of purposes, such as probe design, management of data, analysis, and instrument operation. (See, e.g., U.S. Pat. Nos. 5,593,839; 5,795,716; 5,733,729; 5,974,164; 6,066,454; 6,090,555; 6,185,561; 6,188,783; 6,223,127; 6,229,911 and 6,308,170). Additionally, embodiments may include methods for providing biological information over networks such as the internet, as disclosed in, for instance, U.S. Patent Application Publication Nos. 2003/0097222; 2002/0183936; 2003/0100995; 2003/0120432; 2004/0002818; 2004/0126840 and 2004/0049354.

I. Definitions

Unless defined otherwise, all technical and scientific terms used herein have the same meaning as commonly understood by one of ordinary skill in the art to which the invention pertains. The following definitions supplement those in the art, are directed to the current application, and are not to be imputed to any related or unrelated case, e.g., to any commonly owned patent or patent application. Accordingly, the terminology used herein is for the purpose of describing particular embodiments only, and is not intended to be limiting.

Throughout this disclosure, various aspects of the invention may be presented in a range format. It should be understood that when a description is provided in range format, this is merely for convenience and brevity, and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 2, from 1 to 2.5, from 1 to 3, from 1 to 3.5, from 1 to 4, from 1 to 4.5, from 1 to 5, from 1 to 5.5, from 2 to 4, from 2 to 6, and from 3 to 6 for example, as well as individual numbers within that range, for example, 1, 1.5, 2, 2.5, 3, 3.5, 4, 4.5, 5, 5.5, and 6. This applies regardless of the breadth of the range.

As used in this specification and the appended claims, the singular forms "a," "an" and "the" include plural referents unless the context clearly dictates otherwise. Thus, for example, reference to "a molecule" includes a plurality of such molecules, and the like.

The term "about" as used herein indicates the value of a given quantity varies by +/−10% of the value, or optionally +/−5% of the value, or in some embodiments, by +/−1% of the value so described.

The term "biotin" as used herein refers to the naturally occurring vitamin and also analog, derivative, and other modified forms which are suitable for the application in which the term is employed, whether or not one or more modified forms are expressly mentioned.

The term "biotin binding protein" as used herein refers to any suitable protein capable of binding with biotin with a binding affinity and specificity sufficiently high for the application in which the term is employed, and which thus may vary depending on the particular application. This reference applies whether or not one or more modified forms are expressly mentioned. Non-limiting examples include avidin, streptavidin, analogs, derivatives and other modified forms thereof.

The term "label" as used herein refers to a molecule or combination of molecules which facilitate detection of another molecule or combination of molecules. The label may be a detectable chemical or biochemical moiety or a signal obtained from an enzyme-linked assay. The label molecule(s) can be applied directly to the label target or indirectly through the use of two or more sets of molecules.

The terms "polynucleotide" and "nucleic acid" as used herein are used interchangeably and encompass any physical string of monomer units that can correspond to a string of nucleotides, including a polymer of nucleotides (e.g., a typical DNA or RNA polymer), peptide nucleic acids (PNAs), modified oligonucleotides (e.g., oligonucleotides comprising nucleotides that are not typical to biological RNA or DNA, such as 2'-O-methylated oligonucleotides, LNA, etc.), and the like. The nucleotides of the polynucleotide can be deoxyribonucleotides, ribonucleotides or nucleotide analogs, can be natural or non-natural, and can be unsubstituted, unmodified, substituted or modified. The nucleotides can be linked by phosphodiester bonds, or by phosphorothioate linkages, methylphosphonate linkages, boranophosphate linkages, or the like. The polynucleotide can optionally further comprise non-nucleotide elements such as labels, quenchers, blocking probes, or the like. The polynucleotide can be, e.g., single-stranded or double-stranded.

A "polynucleotide sequence" or "nucleotide sequence" or "nucleic acid sequence" as used herein are used interchangeably and encompass polymers of nucleotides (e.g., an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

A "protecting group" or "protective group" as used interchangeably herein refers to any moiety or molecule designed to block a reactive site in a molecule. A protecting group may be a material which is chemically bound to a reactive functional group on a monomer unit or polymer and which may be removed upon selective exposure to an activator such as a chemical activator, or another activator, such as electromagnetic radiation or light (e.g., ultraviolet or visible light). Protecting groups that are removable upon exposure to electromagnetic radiation (e.g., ultraviolet or visible light) are referred to herein as protecting groups that are "photolabile" or "photolyzable." Other protecting groups, however, employ a different mechanism for deprotection, such as the use of acid or base to deprotect the relevant molecule. Still other protecting groups employ hydrogenolysis for deprotection. Examples of suitable protecting groups for certain embodiments include those described in "Protecting Groups," Phillip J. Kocieński, Thieme (3rd Ed. 2005); "Greene's Protecting Groups in Organic Synthesis," Peter G. M. Wuts and Theodora W. Greene, Wiley-Interscience (4th Ed. 2006); "Handbook of Synthetic Photochemistry," Angelo Albini and Maurizio Fagnoni (Eds.), Wiley-VCH (2010); U.S. Pat. No. 6,147,205 to McGall et al.; U.S. Pat. No. 7,547,775 to Kuimelis et al.; U.S. Patent Application Publication No. 2011/0028350; U.S. Patent Application Publication No. 2003/0040618 to McGall et al.; and U.S. Patent Application Publication No. 2006/0147969 to Kuimelis et al., all of which are incorporated herein by reference in their entireties for all purposes, and particularly for their disclosed protecting groups and related methods of manufacture and use. The proper selection of protecting groups for a particular synthesis is governed by the overall methods employed in the synthesis.

The term "support" or "substrate" as used interchangeably herein refers to a material or group of materials, comprising one or more components, with which one or more molecules are directly or indirectly bound, attached, synthesized upon, linked, or otherwise associated. A support may be constructed from materials that are biological, non-biological, organic, inorganic or a combination of these. A support may be in any suitable size or configuration based upon its use within a particular embodiment.

The term "target" as used herein refers to a molecule of interest within an assay. Targets may be naturally occurring or synthetic, or a combination. Targets may be unaltered (e.g., utilized directly within the organism or a sample thereof), or alternated in a manner appropriate for the assay (e.g., purified, amplified, filtered). Targets may be bound through a suitable means to a binding member within certain assays. Non-limiting examples of targets include, but are not restricted to, antibodies or fragments thereof, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Target may be any suitable size depending on the assay, as nucleic acid targets may merely be a single nucleotide (or a component thereof, such as the base, sugar or phosphate group) and polypeptide targets may merely be a single amino acid (or a component thereof, such as the amine, carboxylic acid or side-chain group).

II. Specific Embodiments
Creation of Functionalized Substrates

Various embodiments disclosed herein may be utilized in association with substrates which have one or more surfaces functionalized with an appropriate functional group. Non-limiting examples of functional groups include aldehyde, alkene, alkyne, amine, aminooxy, azide, carbonyl, carboxyl, carboxylate, disulfide, halogen, hydrazine, hydroxyl, isocyanate, isothiocyanate, sulfate, sulfonate, thiol and thiocarboxyl functional groups. Other suitable functional groups may also be utilized within certain embodiments, such as modified forms of the preceding examples (e.g., activated or protected forms). Various applications may, for example, covalently attach these functionalized silicon compounds to a surface of the substrate, thus forming a functionalized surfaced for subsequent use. For example, a silicon compound with hydroxyl functional groups may be attached to a silicon dioxide substrate, such as a wafer, slide, bead, or microparticle, to provide a functionalized surface. This functionalized surface may subsequently be utilized within the attachment of other molecules, such as nucleic acid monomers, peptide monomers, polynucleotides, and polypeptides, to the surface. For instance, such a surface may be utilized within the creation of a nucleic acid array, such as a high density array, through the covalent attachment and immobilization of nucleic acids or nucleic acid monomers to the functionalized surface.

As used herein, a support or a substrate refers to any suitable material or combination of materials onto which molecules, such as the non-limiting examples recited above of polynucleotides or polypeptides, are synthesized, attached, or otherwise bound. In addition, the substrate may comprise a single component of one or more materials, or multiple components which are utilized together (e.g., assembled into a single substrate component). In many embodiments, the material is rigid or at least semi-rigid, and often has at least one surface that is substantially flat or planar. However, other surfaces on the substrate may not be flat or planar, as may be desirable for manufacturing or subsequent use of the substrate. Furthermore, other embodiments do not utilize flat or planar surfaces. For example, certain embodiments utilize substrates with a surface that possesses physical features such as wells, raised regions, etched trenches, or other features that may be inherent to the substrate material(s). Other embodiments may employ substrate conformations such as particles, microparticles, strands, precipitates, gels, sheets, tubes, spheres, containers, capillaries, pads, slices, films, plates, slides or other conformations known in the art. In other embodiments, substrate conformations of tubes, capillaries or microcapillaries are employed. These embodiments can offer higher surface area to volume ratios compared to certain other embodiments while providing benefits such as reagent reduction and improving thermal transfer efficiency. In addition, some embodiments will utilize physical features in association with the substrate that are only temporary, such as beads that are attached or otherwise associated with a substrate surface and which are released during the overall manufacturing process which utilizes the substrate.

The support or substrate may comprise one or more components of any suitable material(s), including the non-limiting examples of fused silica, fused quartz, glass, Si, $SiO_2$, $SiN_4$, other silicon based materials, Ge, GeAs, GaP, polyvinylidene fluoride, polycarbonate, other polymers, and combinations of these and other suitable materials known in the art. The suitability of substrate material(s) will depend on various factors, such the manufacturing approach to be utilized, assay conditions to which the substrate will be exposed, and other factors. For example, if photolithography is employed for in situ synthesis of oligonucleotides on a functionalized surface of a substrate, then silicon based materials, such as those utilized in the semiconductor and microprocessor industries, may be appropriate for certain embodiments. The appropriateness of material(s) will depend on multiple factors. For example, within the previous example of silicon based substrate materials, such as silicon dioxide, this is utilized with photolithography, certain embodiments may favor a substrate that is transparent or substantially transparent to enable efficient and effective illumination from either side of the substrate (e.g., the side of the substrate with the functionalized surface, or the opposite side of the substrate). A non-limiting example of such a substrate is a wafer of fused silica that is utilized as the substrate. In one particular non-limiting embodiment, the wafer ranges in size from about 1" by about 1" to about 12" by about 12", and a thickness from about 0.5 mm to about 5.0 mm. Such a wafer may be subdivided during the manufacturing process to create multiple subunits, such as the creation of multiple arrays by dicing the wafer into subdivisions. For instance, the diced subunits may measure from about 0.2 cm by about 0.2 cm to about 5.0 cm by about 5 cm. A non-limiting example is a wafer that is 5" by 5" that is diced into 49 subunits of 1.28 cm by 1.28 cm. The size of the starting wafer utilized as the substrate and the size of the subunits will depend on various factors, such as the manufacturing approach employed, the desired characteristics of the final substrate subunits, and assay requirements. See, e.g., U.S. Pat. Nos. 5,143,854; 5,959,098; and 7,332,273, all of which are expressly incorporated by reference herein for all purposes.

Other suitable substrate formats may be utilized, as are appropriate for the manufacturing approach and assay at issue. For example, microparticles may be utilized in certain embodiments. Non-limiting examples of microparticles, methods of manufacturing them, and methods and systems for detecting them and employing them in various assays can be found in, for example, U.S. Pat. Nos. 7,745,091 and 7,745,092 to True; U.S. Patent Application Publication No. 2010/0297448 to True et al.; and U.S. Patent Application Publication Nos. 2010/0227279, 2010/0227770, and 2009/0149340 to True, all of which are expressly incorporated by reference herein for all purposes.

Another substrate format which some embodiments employ is an aerogel, such as a silica or carbon based aerogel which is utilized as the substrate, a portion of a substrate, as a component of a substrate, etc. Aerogel substrates may be used as free standing substrates or as a surface coating for another rigid substrate. Aerogel substrates provide the advantage of large surface area for polymer synthesis. For example, a 1 $cm^2$ portion of an aerogel substrate can possess a total useful surface area of 100 to 1000 $cm^2$ (e.g., 400 to 1000 $m^2/g$). Such aerogel substrates may be prepared by any suitable method known in the art. For example, in one embodiment, a silica aerogel substrate is prepared by the base catalyzed polymerization of $(MeO)_4Si$ or $(EtO)_4Si$ in an ethanol/water solution at room temperature. Porosity and other applicable properties may be adjusted by any suitable change to manufacturing known in the art, such as appropriate alterations to reaction conditions.

The derivatization of substrates with functional groups may occur through any suitable means known in the art. For example, silanation reagents for the silanation of substrates are well known. Such silanation can, for example, prepare substrates with functional groups that can be further derivatized or otherwise utilized for various purposes, such as providing functional groups with which to prepare polynucleotide or polypeptide arrays on the substrate. For example, N-(3-triethoxysilylpropyl)-4-hydroxybutyramide (PCR Inc., Gainesville, Fla. and Gelest Inc., Tullytown, Pa.) has been used to silylate a glass substrate prior to photochemical synthesis of arrays of oligonucleotides on the substrate, as described in McGall et al., J. Am. Chem. Soc., 119: 5081-5090 (1997), which is incorporate herein by reference in its entirety. Hydroxyalkylsilyl compounds have been used to prepare hydroxyalkylated substrates, such as fused silica wafers. N,N-Bis-(hydroxyethyl)aminopropyl-triethoxysilane (BHAPTES) has been used to treat glass substrates to permit the synthesis of high-density oligonucleotide arrays. McGall et al., Proc. Natl. Acad. Sci., 93: 13555-13560 (1996); and Pease et al., Proc. Natl. Acad. Sci., 91: 5022-5026 (1994), which are both incorporated herein by reference in their entireties. Acetoxypropyl-triethoxysilane has been used to treat glass substrates to prepare them for oligonucleotide array synthesis, as described in International Patent Publication No. WO 97/39151, which is incorporated herein by reference in its entirety. 3-glycidoxy propyltrimethoxysilane has been used to treat a glass substrate to provide a linker for the synthesis of oligonucleotides, see, e.g., EP Patent No. 0 368 279, which is incorporated herein by reference in its entirety. Many other silanation reagents and approaches for employing them are known in the art, and are appropriate for use with various embodiments disclosed herein. Certain silanation reagents are purposefully sterically hindered for the creation of more stable surfaced bonded silicon compounds. See, e.g., Kirkland et al., Anal. Chem. 61: 2-11 (1989); and Schneider et al., Synthesis, 1027-1031 (1990). However, such sterically hindered reagents are often more difficult to bond to the substrate as their hindered nature reduces their reactiveness with the substrate.

Additionally, silanes can be prepared which have protected or masked functional groups. Such silanes can be readily purified by, e.g., distillation, and employed in suitable silanation methods, such as gas-phase deposition of a surface of a substrate. After appropriate silanation of a substrate with these silanes, the functional groups can be deprotected through an appropriate manner based upon the type and design of the protection. For example, a silane such as acetoxyalkylsilane, acetoxyethyltrichlorosilane, or acetoxypropyltrimethoxysilane can be deprotected after application using an appropriate method, such as vapor phase ammonia and methylamine or liquid phase aqueous or ethanolic ammonia and alkylamines. Many other silanes may be employed and appropriately deprotected, such as epoxyalkylsilanes (e.g., glycidoxypropyltrimethoxysilane) deprotected using vapor phase HCl or trifluoroacetic acid, or alternatively with liquid phase dilute HCl.

Following application of the silane reagents to form a silane layer, the silanated substrate may be baked to polymerize the silanes on the surface of the substrate and improve the reaction between the silane reagent and the substrate surface. The characteristics of the baking will vary depending on the particular embodiment, the silanes at issue, the substrate and the desired characteristics of the resulting substrate. A non-limiting example of baking conditions suitable for certain embodiments include a temperature in the range of from 90° C. to 120° C., for example 110° C., and a time period of from about 1 minute to about 120 minutes, for example for 60 minutes. This non-limiting example should not be construed to be limiting, as other embodiments may employ conditions within these ranges (e.g., temperatures of 95° C., 110° C.; time periods of 5 minutes, 30 minutes, or 90 minutes) as well as conditions outside of these ranges (e.g., temperatures of 80° C., 125° C.; time periods of 30 seconds, 145 minutes, 160 minutes).

The silanation reagents may be brought into contact with a surface of a substrate through any suitable method. Non-limiting examples of suitable methods include vapor deposition or spray methods. These methods may involve, for example, the volatilization or atomization of a silane solution into a gas phase or spray, followed by deposition of the gas phase or spray upon the surface of the substrate, often by ambient exposure of the surface of the substrate to the gas phase or spray. Vapor deposition typically results in a more even application of the derivatization solution than simply immersing the substrate into the solution. The efficacy of the derivatization process, e.g., the density and uniformity of functional groups on the substrate surface, may generally be assessed by adding a fluorophore which binds to the functional groups. For example, a phosphoramidite with a suitable fluorescent label can be reacted with the functional groups, and the resulting fluorescent across the surface of the substrate analyzed to assess efficacy.

Creation of Polymer Arrays

Creation of polymer arrays of different biological polymer sequences, such as nucleic acid and polypeptide arrays, through a variety of techniques is well known. See, e.g., U.S. Pat. No. 5,143,854 to Pirrung et al.; U.S. Pat. No. 5,744,305 to Fodor et al.; U.S. Pat. No. 7,332,273 to Trulson et al.; U.S. Pat. No. 6,242,266 to Schleifer et al.; U.S. Pat. No. 6,375,903 to Cerrina et al.; U.S. Pat. No. 5,436,327 to Southern et al.; U.S. Pat. No. 5,474,796 to Brennan; U.S. Pat. No. 5,658,802 to Hayes et al.; U.S. Pat. No. 5,770,151 to Roach et al.; U.S. Pat. No. 5,807,522 to Brown et al.; U.S. Pat. No. 5,981,733 to Gamble et al.; and U.S. Pat. No. 6,101,946 to Martinsky, all of which are expressly incorporated herein by reference for all purposes. Such arrays may contain hundreds, thousands, or millions of different polynucleotide or polypeptide sequences, depending upon, for example, the abilities of the particular manufacturing technique at issue with respect to feature density, the size of the relevant solid support of silicon, glass, or other material, the desired characteristics of the relevant assay, and other factors. Within the non-limiting example of nucleic acid arrays, probes of polynucleotides may range from, for example, 10-200 nucleotides in length., such as 10, 15, 25, 30, 35, 40, 45, 50, 65, 70, 75, 100, 125, 150, or 200 nucleotides. This range should not be construed to be limiting, as depending on the manufacturing approach, assay characteristics, and many other factors, nucleic acid arrays may include probes within this range not explicitly mentioned above, such as 28, 49, or 79 nucleotides in length, or probes outside of this range, such as 9 nucleotides or 250 nucleotides.

Certain embodiments may utilize arrays created through Very Large Scale Immobilized Polymer Synthesis (VLSIPS) technology for synthesizing oligonucleotides and oligonucleotide analogues on substrates. The oligonucleotide is typically linked to the substrate via the 3'-hydroxyl group of the oligonucleotide and a functional group on the substrate which results in the formation of an ether, ester, carbamate or phosphate ester linkage. Nucleotide or oligonucleotide analogues are attached to the solid support via carbon-carbon bonds using, for example, supports having (poly)trifluorochloroethylene surfaces. Siloxane bonds or other appropriate attachment techniques may also be utilized. For example, siloxane bonds may be formed through reactions of surface attaching portions which possess trichlorosilyl or trialkoxysilyl groups. The surface attaching groups additionally possess functional groups (e.g., amine, hydroxyl, thiol, carboxyl) for attachment of an oligonucleotide analogue portion. Non-limiting examples of surface attaching portions include aminoalkylsilanes and hydroxyalkylsilanes. Non-limiting examples of the surface attaching portion of the oligonucleotide analog include bis(2-hydroxyethyl)-amino-propyltriethoxysilane, aminopropyltriethoxysilane and hydroxypropyl triethoxysilane.

Labeling Compounds

Many applications in life science research and medical diagnostics employ one or more types of labels to detect biomolecules of interest, such as nucleic acids with particular nucleotide sequences or polypeptides with particular amino acid sequences. Such applications include many different types of assays and are used with various technologies, instruments, reagents, etc. For example, with respect to the analysis of nucleic acids, labels are utilized within assays which employ microarrays, sequencing, real-time polymerase chain reaction and many other approaches. Various assays employ suitable labels of various compositions and detected through appropriate spectroscopic, photochemical, biochemical, immunochemical, electrical, optical or chemical means. Commonly employed labels include fluorescent, luminescent, chemiluminescent, light-scattering, and colorimetric varieties. Labels can be applied directly to a particular target or indirectly (e.g., through the use of two or more sets of molecules, via an antibody, via enzymatic labeling systems). Commonly used types of fluorescent labels include organic dyes (e.g., fluorescein, Cy3, Cy5, rhodamine), biological fluorophores (e.g., phycoerythrocyanin), and quantum dots (e.g., a carboxyl quantum dot). Fluorescent labels may include, for example, N-hydroxysuccinimide ester activated dyes that react with exposed amino groups, malemide activated dyes that react with sulfhydryl groups, phosphine activated dyes that react with azide groups, or other suitable labels known in the art. Such labels are available commercially from, for example, Invitrogen (Carlsbad, Calif.), Thermo Fisher Scientific (Waltham, Mass.), and ATTO-TEC GmbH (Siegen, Germany). Antibody labeling techniques include the use of radiolabels (e.g., removing phosphate groups with an alkaline phosphatase and replacing the group with a radioactive phosphate group), enzymatic tags (e.g., horseradish peroxidase), and fluorescent tags (e.g., utilizing an anti-streptavidin biotinylated antibody with streptavidin phycoerythrin).

Assays for the detection of nucleic acids through hybridization with a microarray often employ one or more labels. These labels may be directly or indirectly attached, incorporated or otherwise associated through various means in the art to the sample nucleic acids. For example, within assays utilizing amplification during sample preparation, one or more labels may be incorporated during one or more amplification steps. This may involve, for instance, the use of polymerase chain reaction (PCR) with labeled primers and/or nucleotides to provide a labeled amplification product. Alternative approaches include the addition of a label to the original nucleic acid sample (e.g., when no amplification is performed), or to the amplification product. For example, these approaches may include nick translation labeling to introduce labeled nucleotides, using a kinase to remove the phosphate from the end of a nucleic acid fragment and subsequently incorporate a labeled phosphate (e.g., a radioactive phosphate), end-labeling using a biotin-labeled deoxynucleotide analog with a terminal deoxynucleotidyl transferase with subsequent use of labeled streptavidin, end-labeling through utilization of a ligase to incorporate a label, or many other approaches known in the art. Patents with additional non-limiting examples of suitable labels and methods of using them include U.S. Pat. Nos. 6,864,059; 6,965,020; 7,423,143; 6,864,059; 7,468,243; 7,491,818; 3,817,837; 3,850,752; 3,939,350; 3,996,345; 4,277,437; 4,275,149; and 4,366,241, all of which are incorporated herein by reference in their entirety for all purposes. For a review of methods of labeling nucleic acids and detecting labeled hybridized nucleic acids, see Laboratory Techniques in Biochemistry and Molecular Biology, Vol. 24: Hybridization with Nucleic Acid Probes, P. Tijssen, ed. Elsevier, N.Y., (1993).

Means of detecting such labels are well known to those of skill in the art. For example, radiolabels may be detected using photographic film or scintillation counters. Fluorescent labels may be detected using a photodetector to detect fluorescent emissions after appropriate excitation. Enzymatic labels are typically detected by providing the enzyme with a substrate and detecting the reaction product produced by the action of the enzyme on the substrate, and colorimetric labels are detected by simply visualizing the colored label.

Suitable labels may be employed in a "direct" or "indirect" fashion. Direct labels include those that are directly attached, bound, incorporated, etc. into the target molecule, such as a nucleic acid or polypeptide from a sample from an organism of interest. Thus, as a non-limiting example, if a nucleic acid sample is to be analyzed through the use of a microarray, a direct labeling strategy may bind or incorporate labels into the nucleic acids of the sample before hybridization with the microarray.

Conversely, indirect labels include those that are attached, bound, incorporated, etc. into the target molecule in an indirect fashion, such as through an intermediary molecule. A non-limiting example well known in the art is to biotinylate nucleic acids before subsequent use, such as hybridization with a microarray. Then, the addition of, for example, a streptavidin conjugated fluorophore, will cause indirect binding of the label to the nucleic acids of interest for subsequent detection. Of course, many other label types may be employed, and other biotin binding techniques may be employed, such as utilizing avidin, streptavidin, deglycosylated avidin with modified arginines, avidin with a tyrosine binding site that has been nitrated or iodinated, anti-biotin antibodies, or other biotin-binding moieties. Furthermore, continuing with the non-limiting example of biotinylation, the use of variants and analogs is also possible if they retain sufficient binding affinity for a particular assay. A non-limiting example is desthiobiotin, which retains high affinity with respect to, for instance, streptavidin.

Caged Binding Member Compounds and Methods of Making and Using

Many approaches are known in the art for caged binding member compounds and methods of making and using, such as those which protect a binding member to reduce or eliminate the affinity the binding member possesses for a particular target binding species (relative to the affinity the binding member would possess in its uncaged state for the target binding species). These approaches can be utilized to prevent binding of a member with undesired targets which are otherwise capable of binding with the member, or for other purposes such as controlling the time and location of binding. Additionally, a variety of approaches can be utilized to ensure that the affinity of the binding member for the target binding species is not reduced, at least not substantially, after uncaging (as compared to the affinity possessed without the involvement of caging). For instance, a non-limiting example within the process of manufacturing polymer arrays through photolithography is the protection of otherwise reactive functional groups with photolabile protecting groups (e.g., MeNPOC, NNPOC, NPPOC). These functional groups are then activated for coupling with monomers within certain regions of the substrate through selective illumination, with the light possessing wavelength(s) capable of photolyzing the photolabile protecting groups and freeing the previously protected, or caged, hydroxyl groups. This approach of protecting binding members within a cage is certainly not limited to photolithographic synthesis of nucleic acid arrays, and many variations and adaptations of the concept are well known in the art for use with a variety of molecules, such as nucleic acids, amino acids, antibodies, etc. in a variety of approaches, chemistries, and applications.

Certain embodiments herein utilize this concept with respect to photoprotection of biotin moieties. Specifically, a biotin molecule (or variant or analog thereof) is modified or otherwise altered such that it possesses one or more photoactivatable protecting groups. These protecting groups serve to significantly reduce the binding affinity that the modified biotin molecule possesses for avidin (or variants or modified versions thereof, such as streptavidin) compared to the unmodified state of the biotin molecule. Some embodiments employ a photoactivatable protecting group such that appropriate illumination removes the protecting group to uncage the biotin and restore its natural binding affinity for the appropriate avidin molecule at issue. As a non-limiting example, certain embodiments will utilize protective caging groups that subject to photolysis by illumination in the ultraviolet spectrum (e.g., illumination containing a wavelength of 365 nm).

Alternative embodiments employing protected biotin are also possible. For instance, if avidin is employed to capture a biotin associated target, such capture can be prevented while the biotin molecules are still protected within their cages. Selective removal of the cages to unprotect the biotin at the desired time, location, etc. allows capture of the biotin associated target by the avidin. A non-limiting example would be the use of avidin immobilized on a support to capture biotinylated antibodies, nucleic acids, or proteins.

Photoprotection of a molecule, such as biotin, is generally achieved through modification of the molecule with a photoactivatable protecting group, with the protecting group located at a critical position (e.g., deactivating a particular bond) to prevent undesired reactions while the molecule is still caged by the protecting group. The inactive, caged molecule is then uncaged through appropriate irradiation, such as illumination at one or more appropriate wavelengths. A common example of such illumination is ultraviolet light. For embodiments where the protected molecule is associated with molecules that might be damaged by shorter wavelengths within the ultraviolet spectrum (e.g., potential damage to DNA by using illumination with wavelengths shorter than 340 nm), longer wavelengths are more appropriate (e.g., 350 nm, 360 nm, 365 nm, 375 nm, 390 nm). For additional background material, see Lusic and Deiters, "A New Photocaging Group for Aromatic N-Heterocycles," Synthesis, 2006, No. 13, pp 2147-2150 and Lusic et al., "Photochemical DNA Activation," Organic Letters, 2007, Vol. 9, No. 10, 1903-1905, which describe nucleobase caging with 6-nitropiperonyloxymethyl (NPOM) groups, and which are incorporated herein by reference in their entireties for all purposes.

Many approaches are available for the caging of polymers such as oligonucleotides with photolabile protecting groups. For example, the caging protecting group may be placed on internucleotide phosphates, various positions on the sugar, or the nucleobase. Certain approaches incorporate biotin during phosphoramidite synthesis of the oligonucleotides. For background regarding the use of biotin, particularly caged protected biotin, see U.S. Pat. Nos. 5,252,743; 5,451,683; 6,919,211; and 6,955,915; U.S. Patent Application Publication No. 2003/0119011; and Pirrung and Huang, "A General Method for the Spatially Defined Immobilization of Biomolecules on Glass Surfaces Using "Caged" Biotin," Bioconjugate Chem., (1996) 7(3): 317-321, all of which are incorporated herein by reference in their entireties for all purposes.

Figure 1B:
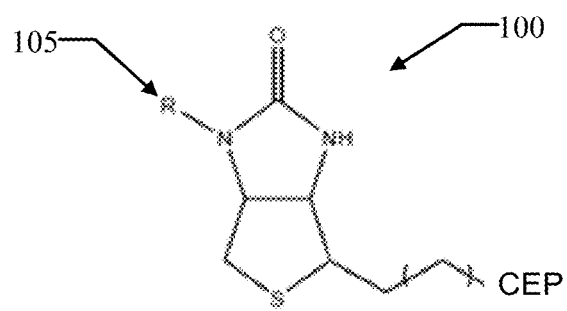
FIG. 1(B) illustrates a non-limiting example of biotin with a protecting group and a cyanoethyl phosphoramidite.
Figure 1C:
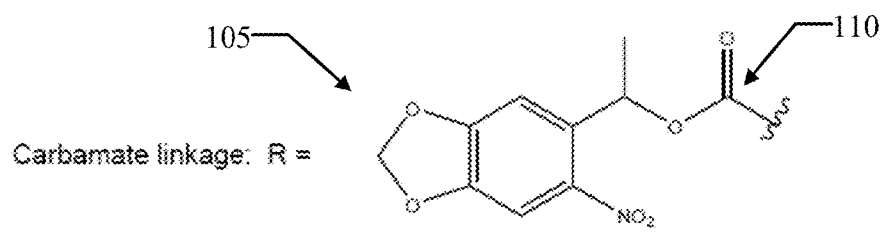
FIG. 1(C) and FIG. 1(D) illustrates two non-limiting examples of potential linkages, carbamate and ether, between biotin and a protecting group.
Figure 1D:
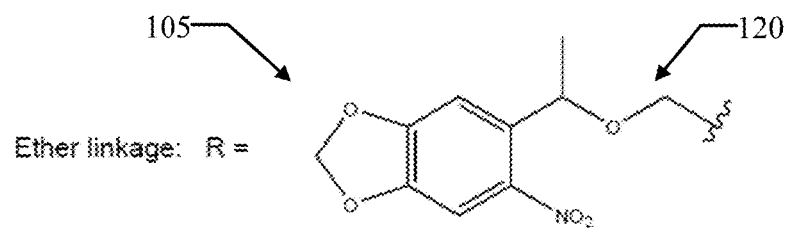

FIGS. 1(A)-1(D) illustrate biotin and protected biotins to be utilized within certain embodiments. FIG. 1(A) depicts a biotin 100. FIG. 1(B) depicts a biotin 100 with a protecting group 105 (designated as "R") and a cyanoethyl phosphoramidite "CEP" (e.g., the nucleoside phosphoramidite as would be utilized in oligonucleotide synthesis). It should be carefully noted that although the FIG. 1(B) includes a cyanoethyl phosphoramidite in association with the depicted protected biotin, many embodiments herein will not. Instead, these embodiments many employ different molecules in connection with the valeric acid substituent of the tetrahydrothiophene ring as may be required or desirable within certain embodiments. FIGS. 1(B)-1(C) depict examples of the protecting group 105 from FIG. 1(B). The non-limiting example of a protective group which is depicted in FIGS. 1(C)-1(D) is 6-nitropiperonyloxymethyl (NPOM). Protected biotin is particularly useful as in its protected state, its affinity for avidin targets (e.g., streptavidin) is greatly reduced, but its naturally high binding affinity will return once appropriate deprotection is performed.

As can be seen in FIG. 1(C), a carbamate linkage 110 connects the protecting group 105 of NPOM to the biotin 100, while FIG. 1(D) depicts an ether linkage 120 which connects the protecting group 105 of NPOM to biotin 100. The carbamate linkage 110 within FIG. 1(C) is common to many photolabile nitrogen protecting groups, but possesses disadvantages for many applications. For example, carbamate linkages are susceptible to undesired hydrolysis, particularly with respect to aqueous conditions with an elevated pH, which can lead to unintentional deprotection of biotin 100 (e.g., hydrolysis which removes the protecting group that is not mediated by the intended manner of deprotection, such as application of appropriate photolyzing illumination). This can make a carbamate linkage disadvantageous for various applications, including use with amidites (e.g., applications involving phosphoramidite chemistry). The ether linkage 120 in FIG. 1(D), however, resists hydrolysis and thus prevents undesired deprotection until the desired time and location where the appropriate illumination is employed. Thus, a biotin 100 as depicted in FIG. 1(B) with a protecting group 105, such as the non-limiting example of NPOM, utilizing an ether linkage 120 as illustrated in FIG. 1(D), provides a much more stable photoprotected biotin that is significantly more likely to only be deprotected when actually desired and when the appropriate deprotection means are employed.

Figure 2:
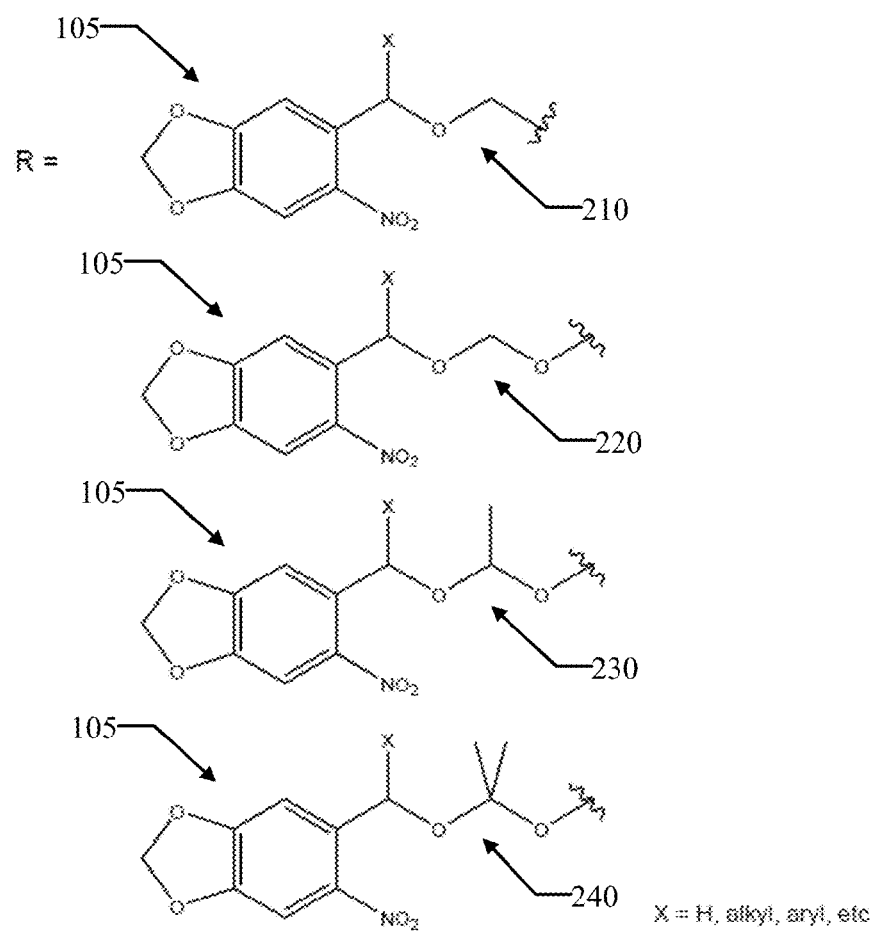
FIG. 2 illustrates non-limiting examples of biotin protecting groups with alternative linkages.

The exact depiction of NPOM with an ether linkage 120, as illustrated in FIG. 1(D), should not be construed to limit the embodiments disclosed herein, as not only other photolabile protecting groups can be used, but also other variants and modifications of linkages can be employed. For example, FIG. 2 provides additional non-limiting examples of protecting groups 105 and their linkages that can be employed with biotin 100. These non-limiting examples include linkage variations 210, 220, 230 and 240. Within these variations, X is any suitable substituent, including but not limited to the non-limiting examples of hydrogen, alkyl groups, and aryl groups. Many additional variations of these non-limiting examples will be evident to one of skill in the art based upon the disclosures herein.

Figure 3:
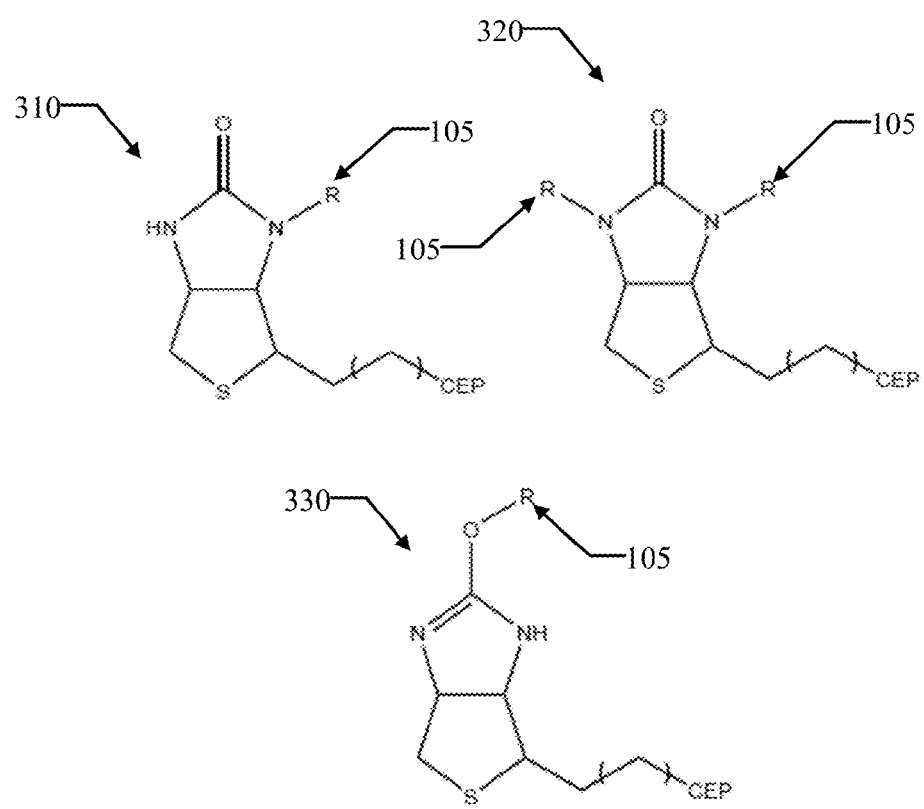
FIG. 3 illustrates non-limiting examples of biotin structural isomers.

FIG. 3 depicts non-limiting examples of suitable biotin molecules 310, 320 and 330 which are protected by one or more protective groups 105. These examples include, for instance, positional isomers of the biotin 100 with a protecting group 105 that is depicted in FIG. 1(B). Additionally, as can be observed within biotin molecule 320, a biotin can be protected by more than one protecting group 105 to ensure that an extremely low affinity for avidin, streptavidin, etc. until the protecting groups 105 are removed. Additionally, appropriate creation of a biotin 320 with two protecting groups allows the incorporation of two distinct protecting groups 105 into a particular biotin 320. Thereafter, careful selection and ordering of deprotecting mechanisms allows removal of only one protecting group 105 for certain biotins within an assay to preserve their low affinity for the appropriate biotin binding protein until such time that the remaining protecting group 105 is also removed.

Figure 4:
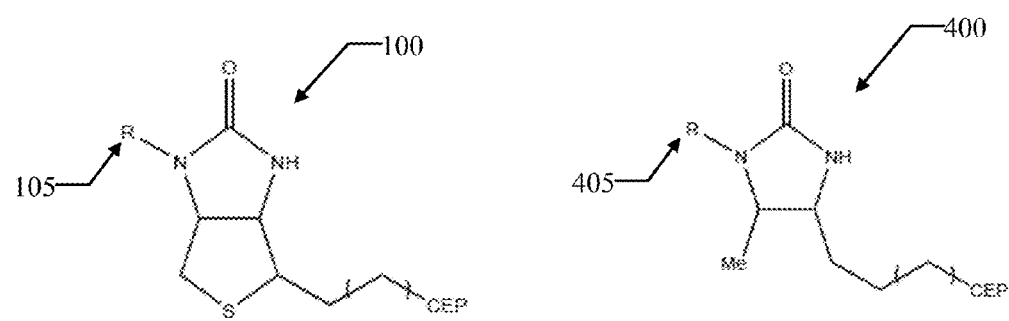
FIG. 4 illustrates a comparison of biotin and desthiobiotin.

FIG. 4 illustrates a comparison of biotin 100 to desthiobiotin 400. Biotin 100 is depicted with a protecting group 105 (designated as "R"). Desthiobiotin 400 may also possess a protecting group 405 (designated as "R"), but the R group may also simply represent H (i.e., desthiobiotin 400 may be utilized in unprotected forms). Desthiobiotin 400 is an additional non-limiting example of a biotin variant that also possesses affinity for avidin, and may be employed in lieu of biotin within many embodiments and their various applications. Certain embodiments combine the use of biotin and desthiobiotin, as is discussed subsequently herein.

Figure 5:
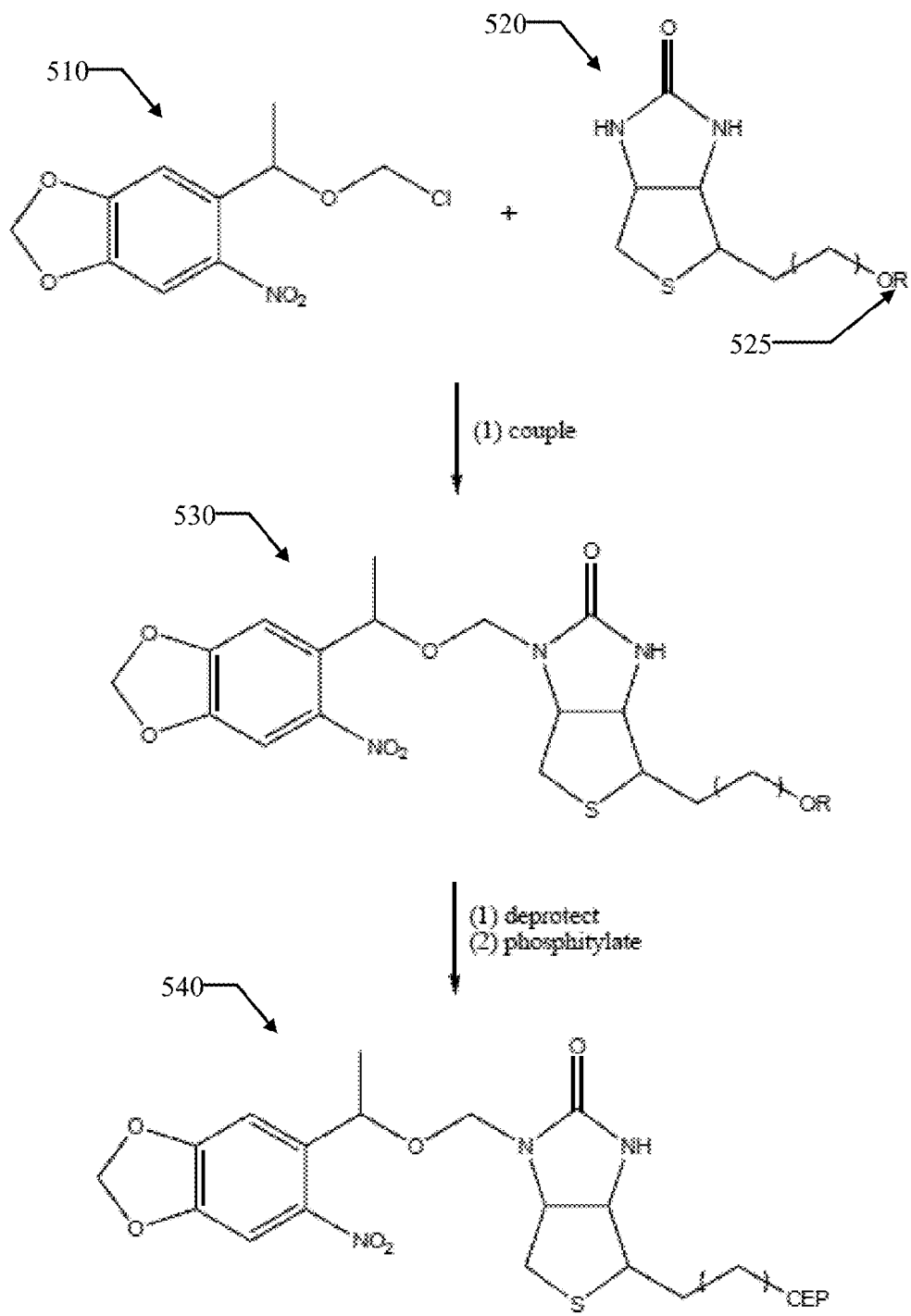
FIG. 5 illustrates a non-limiting example of a synthesis scheme to protect biotin and couple the protected biotin with a cyanoethyl phosphoramidite.

FIG. 5 illustrates a non-limiting synthesis scheme for producing NPOM protected biotin phosphoramidite. First, 6-nitropiperonyloxymethyl chloride (NPOM-Cl) is coupled with biotin 520. Biotin 520 possesses a protective group 525 (designated as "R"), and is any suitable protecting group capable of guiding coupling of NPOM to the tetrahydroimidizalone ring. Subsequently, the NPOM protected biotin 530 is deprotected to remove protective group 525. The final step is phosphitylation to produce the NPOM protected biotin phosphoramidite 540.

Protected biotin can be employed in a variety of labeling and detection approaches. In general, these approaches utilize the protected nature of the biotin prevent binding of avidin (or streptavidin, etc.) to the biotin with the knowledge that with the more stable ether linkage that is greatly more resistant to hydrolysis than, e.g., a more common carbamate linkage, and that the biotin will be protected from potential avidin binding until the desired stage of the relevant assay. As discussed previously herein, biotinylation can occur through a variety of methods known in the art, including chemical and enzymatic means. Proteins can be biotinylated, for instance, through primary amine, sulfhydryl, carboxyl, or glycoprotein biotinylation. Nucleic acids can incorporate protected biotin through nick translation labeling to introduce biotin possessing nucleotides, end-labeling using a biotin-labeled deoxynucleotide analog with a terminal deoxynucleotidyl transferase, end-labeling through utilization of a ligase to incorporate a label, or other suitable approaches known in the art. The biotin is then deprotected at the desirable stage of the assay, and exposed appropriately for detection suitable for the assay (e.g., use of an avidin conjugates such as streptavidin phycoerythrin for subsequent detection of the targets at issue within the assay.

Thus, in addition to the use of protected biotin with non-biotin associated labels, the use of protected biotin can be combined with the use of unprotected biotin to facilitate a multi-color approach without the need for distinct binding pairs for each color. Included within the many embodiments potentially utilizing protected biotin are microarray assays which utilize a two color approach. Background on utilizing a multicolor analysis with microarrays may be found within, for example, Shalon et al., "A DNA microarray system for analyzing complex DNA samples using two-color fluorescent probe hybridization," Genome Res., 6: 639-645 (1996); Yang et al., "Evaluation of experimental designs for two-color cDNA microarrays," J. Comput. Biol., 12(9): 1202-1220 (2005); Nguyen et al., "Experimental designs for 2-colour cDNA microarray experiments," Appl. Stochastic Models Bus. Ind., 22: 631-638 (2006); Yatskou et al., "Advanced spot quality analysis in two-colour microarray experiments, BMC Research Notes, 1: 80 (2008); and Zhu et al., "Assessment of fluorescence resonance energy transfer for two-color DNA microarray platforms," Anal. Chem., 82(12): 5304-5312 (2010). Of course, the use of multicolor analysis is not limited to microarray applications, and embodiments may be utilized within any suitable application, such as nucleic acid sequencing (see, e.g., Metzker, "Sequencing technologies—the next generation," Nature Reviews Genetics, 11: 31-46 (2010)); Ledergerber et al., "Base-calling for next-generation sequencing platforms," Briefings in Bioinformatics, 12(5): 489-497 (2011); and Blow, "DNA sequencing: generation next-next," Nature Methods, 5: 267-274 (2008)), or proteomics applications (see, e.g., Waggoner, "Fluorescent labels for proteomics and genomics," Current Opinion in Chemical Biology, 10(1): 62-66 (2006); Kleiner et al., "Ultra-high sensitivity multi-photon detection imaging in proteomics analyses," Proteomics, 5(9): 2322-2330 (2005)), and many other applications known in the art. All of the preceding references are incorporated herein by reference in their entireties for all purposes.

Figure 6:
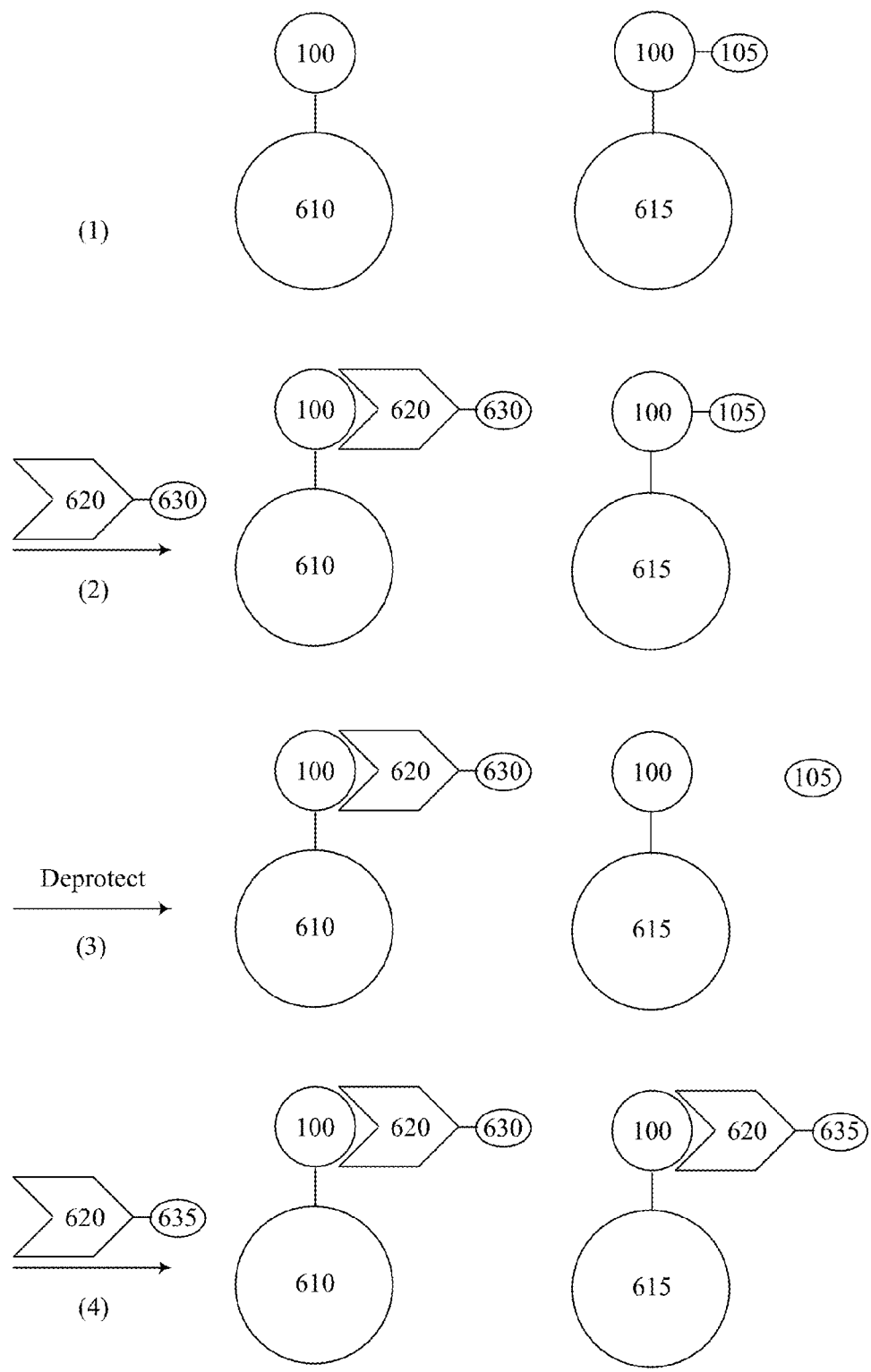
FIG. 6 illustrates a non-limiting example of a labeling scheme incorporating the use of biotin with protected biotin.

FIG. 6 depicts a non-limiting example of a general labeling scheme for utilizing multiple types of labels through the use of biotin with protected biotin that can be employed in many different applications, as will be apparent to one of skill in the art upon reading the disclosure herein. Step 1 depicts the results of biotinylation (through any suitable means, including direct and indirect techniques) of a first target 610 and a second target 615. First and second targets 610 and 615 may be any suitable target, including nucleic acids, proteins, antibodies, cells (e.g., biotinylation of cell surface proteins), and any other suitable target known in the art. Specifically, first target 610 is biotinylated with an unprotected biotin 100 while second target 615 is biotinylated with a biotin 100 possessing a protecting group 105.

Step b 2 of FIG. 6 depicts the addition of an appropriate biotin binding protein 620 which is conjugated with a first label 630. Any suitable biotin binding protein can be employed, including natural, artificial, and modified proteins, which include but are not limited to avidin, streptavidin, recombinant versions thereof, ExtrAvidin® protein (Sigma-Aldrich Corporation, St. Louis, Mo.), NeutrAvidin® protein (Thermo Fisher Scientific, Inc., Waltham, Mass.), CaptAvidin™ protein (Life Technologies Corporation, Carlsbad, Calif.), and other suitable proteins known in the art. First label 630 may be any suitable label as discussed herein and that is desired for the particular labeling scheme at issue, including the aforementioned non-limiting examples of fluorescent, luminescent, chemiluminescent, light-scattering, and colorimetric labels. As seen with Step 2 of FIG. 6, biotin binding protein 620 binds with the unprotected biotin 100 to effectuate labeling of first target 610 with first label 630. Meanwhile, protecting group 105 of the biotin 100 of second target 615 remains unbound to the biotin binding protein 620 and its conjugated label 630.

Step 3 of FIG. 6 depicts the deprotection of the biotin 100 of second target 615. The exact manner of deprotection will depend upon factors such as the particular characteristics of protecting group 105 (e.g., whether protecting group 105 is photolabile, acid-labile, base-labile), the relevant assay conditions, biological and chemical concerns for the various assay components, and other factors known in the art. Step 3 results in the freeing of the biotin 100 of second target 615 of protecting group 105, and thus restoration of the ability for biotin 100 of second target 615 to bind with a suitable biotin binding protein 620. Step 3 may optionally involve, depending on the assay at issue, washing, filtering or separation steps to remove the released protecting group 105.

Step 4 of FIG. 6 depicts the addition of biotin binding protein 620, which is conjugated with a second label 635. Second label 635 is distinguishable from first label 630 under the appropriate detection conditions (as required by the particular characteristics of first and second labels 630 and 635). Thus, second target 615 is labeled with second label 635 through the binding of the added protein conjugated label. This addition, however, does not affect the labeling of first target 610 with the already bound conjugate of biotin binding protein 620 and first label 630. In many embodiments, the particular biotin binding protein 620 employed within Step 4 is the same type of protein utilized within Step 2. In this manner, the same relevant binding pair of biotin 100 and biotin binding protein 620 is employed for both first and second targets 610 and 615, ensuring greater consistency and predictability for the binding scheme in comparison to the use of binding pairs with different binding affinities. However, certain assays may utilize a different biotin binding protein within Step 4 if so desired, because as mentioned above, many suitable biotin binding proteins are known in the art.

Furthermore, many variants of the process depicted within FIG. 6 will be apparent to one of skill in the art. For example, certain assays may desire to amplify the signal of first and second labels 630 and 635. This can be achieved, for instance, through the application in multiple layers of staining, which comprise the addition of biotinylated antibodies which target biotin binding protein 620 and the subsequent addition of addition biotin binding proteins 620 conjugated with the appropriate label. If, for example, the signal of both first and second labels 630 and 635 are to be amplified, then such a variation can employ different types of biotin binding proteins 620 within Steps 2 and 4 respectively. This can thus ensure, through the use of appropriate antibodies specific only for the desired biotin binding protein, the proper amplification of the two labels.

Moreover, the approach illustrated in FIG. 6 can easily be expanded to encompass labeling approaches with more than two types of labels, such as 3, 4, 5, 6, 7, 8, 9, 10 or more types of labels. Such approaches require the use of different protecting groups 105 for each target which is to be labeled with a different label. Thus, if a 4 label approach is to be utilized, at least 3 different protecting groups 105 are employed. By "different" protecting groups, it is meant that the exact manner of deprotection will be different. Thus, for the repetitions of Step 3 in the removal of a particular type of protecting group 105 within a specific assay step, the deprotection mechanism will only remove that particular type. Thus, within the example of a 4 label approach, an unprotected biotin 100 may be employed in combination with: (1) a biotin 100 protected by a photolabile protecting group 105, (2) a biotin 100 protected by an acid-labile protecting group 105, and (3) a biotin 100 protected by a base-labile protecting group. Of course, not each type of protecting group 105 need be removed through an entirely different mechanism. For instance, use of multiple types of photolabile protecting groups is possible if they are associated with at least partially non-overlapping wavelengths capable of effectuating photolysis. Relevant factors which guide selection of the different protecting group include assay concerns such as the available instruments and reagents, assay condition boundaries (e.g., pH or salt limitations which must be observed within various assay stages), and the number of protecting groups. Additionally, as illustrated within FIG. 3, certain biotins may encompass two protecting groups 105. Through the use of different protecting groups 105 for a particular biotin in relation to the combination of other sets of protecting groups 105 for other targets within an assay, the use of the same protecting group 105 can be employed in association with multiple labels as long as the biotin molecules which are not to be bound to a biotin binding protein 620 in that step maintain their other protecting group 105.

Figure 7A:
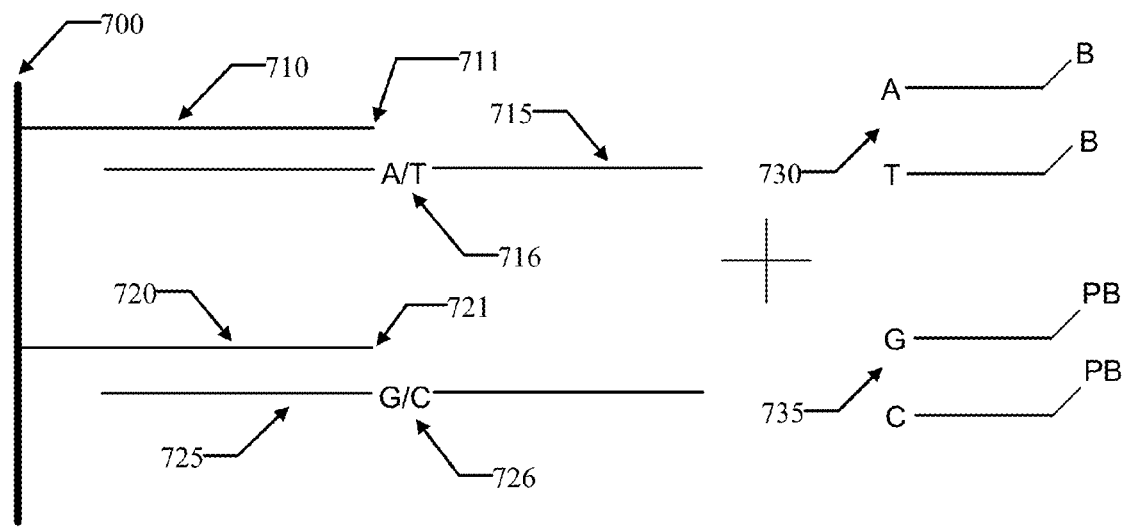
FIGS. 7(A)-7(B) illustrate a non-limiting example of a labeling scheme involving hybridized nucleic acids and ligation with a set of oligonucleotides which possess biotin or protected biotin to facilitate multiple label use.

A non-limiting example of utilizing protected biotin within a multi-label approach is depicted within FIGS. 7(A)-7(D) and 8. In this particular illustration, the labeling is performed through the use of labeling probes which are subsequently incorporated by ligation. The particular labeling method illustrated here, however, should not be construed to limit the embodiments disclosed herein, as any suitable labeling technique known in the art can be suitably adjusted. FIG. 7(A) depicts a support 700 which possesses a first oligonucleotide 710 and a second oligonucleotide 720. First oligonucleotide 710 is designed to hybridize with a portion of target 715 while second oligonucleotide 720 is designed to hybridize with a portion of target 725. First oligonucleotide 710 has a reactive end 711 while second oligonucleotide 720 has a reactive end 721, where reactive end 711 and reactive end 721 are capable of being ligated to a labeled nucleic acid probe. Within this particular labeling example which utilizes two labels, non-hybridized base 716 of target 715 (which is the first base of target 715 that is not hybridized with first oligonucleotide 710) can be either an A or T, while the non-hybridized base 726 (which is the first base of target 725 that is not hybridized with second oligonucleotide 720) of target 725 can be either a G or C.

To support 700 is added a first set of labeled nucleic acid probes 730 and a second set of labeled nucleic acid probes 735. The first set of labeled probes 730 possesses an A or T at the end of the probe capable of ligation with reactive end 711, and also possesses an unprotected biotin 100 (designated as "B"). The remaining bases of labeled probes 730 may be, for example, degenerate or universal bases (e.g., 5-nitroindole). The first set of labeled probes 730 is depicted within FIG. 7(C). The particular illustration of FIG. 7(C) shows 8 universal bases (designated as "N"), but this should not be construed to be limiting, as any suitable number of universal bases may be employed, such as 1-50, including 1, 2, 3, 4, 5, 6, 7, 8, 9, 10, 15, 20, 25, 35, 45 or 50, or an even higher number in certain embodiments. Furthermore, certain embodiments may not employ any universal bases. The second set of labeled probes 735 is similar in many aspects to the first set of labeled probes 730, but with several key distinctions. First, the base of the probes within the second set 735 which is capable of ligation to reactive end 721 is either a G or C. Second, the second set of labeled probes 735 possesses a protected biotin (designated as "PB"). The second set of labeled probes is further illustrated within FIG. 7(D), which depicts the 9-mer, biotin 100, and protecting group 105 (designated as "R"). Protecting group 105 may be, for instance, one of the non-limiting examples provided in FIG. 2, or any other suitable protecting group as guided by the requirements or desirable features of the assay at issue.

Figure 7B:
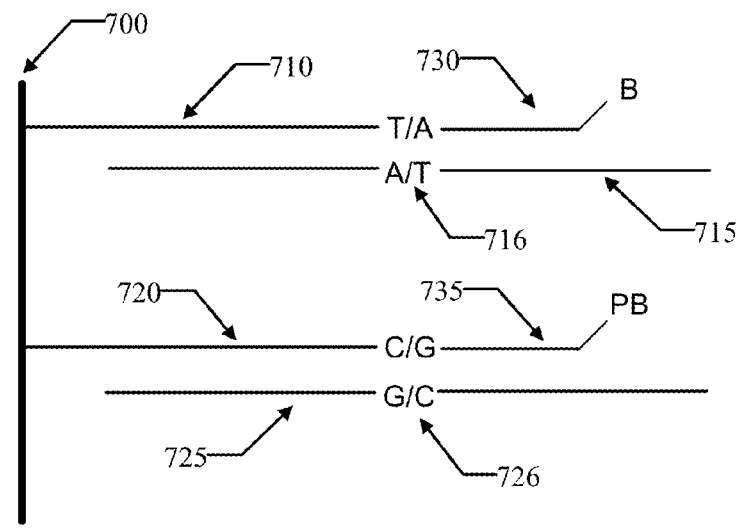
Figure 7C:
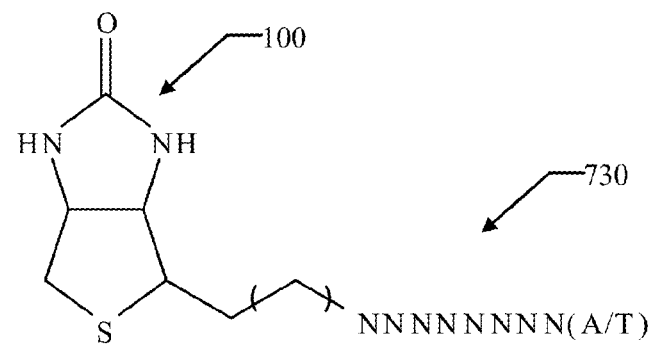
FIGS. 7(C)-7(D) illustrate non-limiting examples of the set of oligonucleotides with either biotin or protected biotin as used within the depiction of FIGS. 7(A)-7(B).
Figure 7D:
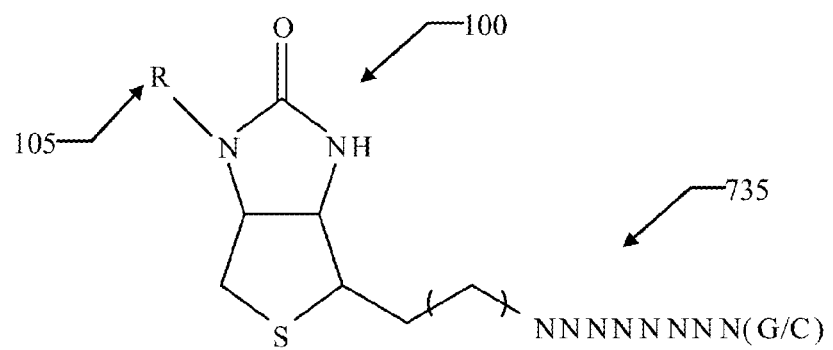

FIG. 7(B) depicts the result of utilizing first oligonucleotide 710 hybridized with first target 715, second oligonucleotide 720 hybridized with second target 725, the first set of labeled probes 730 and the second set of labeled probes 735 with an appropriate ligase capable of mismatch discrimination (e.g., Taq DNA ligase). Based upon the identities of non-hybridized bases 716 and 726, a probe from the first set of labeled probes 730 has ligated to first oligonucleotide 710 while a probe from the second set of labeled probes 735 has ligated to second oligonucleotide 720. This results in first oligonucleotide 710 being labeled with an unprotected biotin while second oligonucleotide 720 is labeled with a protected biotin.

Figure 8:
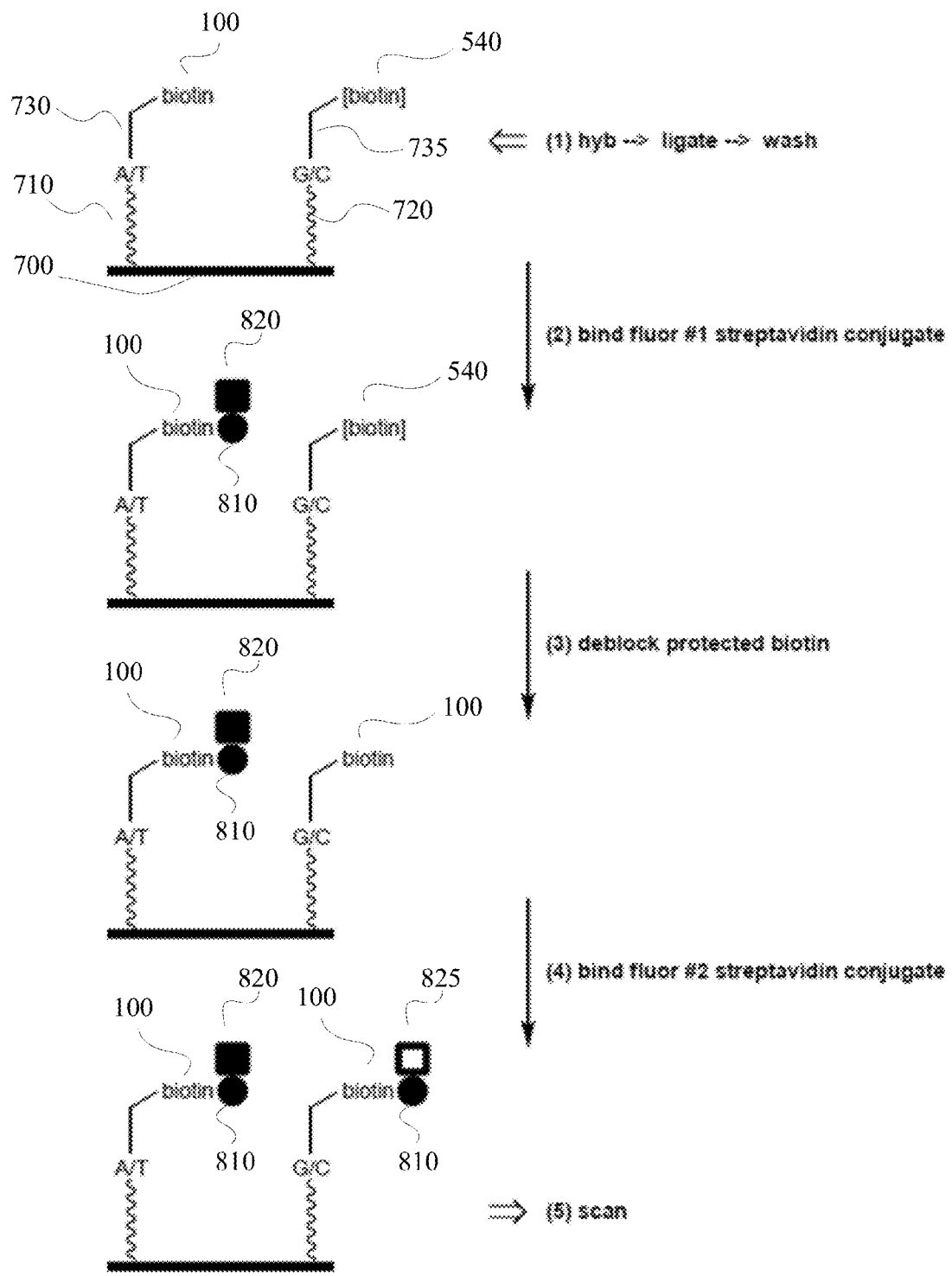
FIG. 8 illustrates a non-limiting example of selectively employing two labels within the example depicted within FIGS. 7(A)-7(D).

FIG. 8 depicts a continuation of the non-limiting example illustrated within FIGS. 7(A)-7(D). Specifically, FIG. 8 begins with the depiction of support 700 as illustrated in FIG. 7(B). Support 700 is shown with first oligonucleotide 710 and second oligonucleotide 720. While not explicitly shown, within this particular non-limiting example, first oligonucleotide 710 is still hybridized with first target 715 and second oligonucleotide 720 is still hybridized with second target 725. Furthermore, as illustrated, first oligonucleotide 710 is ligated with a probe from the first set of labeled probes 730, which contains an unprotected biotin 100, while second oligonucleotide 720 is ligated with a probe from the second set of labeled probes 735, which contains a protected biotin 540. Step 1 of FIG. 7 describes the process partially illustrated within FIGS. 7(A)-7(B), with the hybridization of the oligonucleotides to the targets, the ligation of the labeled probes, and any applicable washing steps (e.g., to remove unligated labeled probes).

Step 2 within FIG. 8 illustrates the binding of biotin 100, which is unprotected, with a suitable biotin binding protein-label conjugate while protected biotin 540 remains unbound to the biotin binding protein-label conjugate. The non-limiting example depicted within Step 2 shows biotin 100 binding with a biotin binding protein-label conjugate, such as with streptavidin 810 conjugated with R-phycoerythrin 820. Other labels, including non-fluorescent labels, are employed in alternative embodiments.

Step 3 within FIG. 8 illustrates the deprotection of protected biotin 540. The exact manner of deprotection will depend upon the protecting group 105 which is employed within a particular embodiment. For example, if NPOM is employed to protect the biotin, deprotection can comprise illumination which includes a wavelength of 365 nm. Other embodiments may utilize photolabile protecting groups which are photolyzable with different wavelengths, or protecting groups which are not photolabile (e.g., the use of a mild acid solution to remove dimethoxytrityl (DMT)). The selection of an appropriate protecting group and its associated manner of deprotection is dependent upon many factors, including whether the deprotection will affect the biotin binding protein-label conjugate already bound to the biotin which was not protected. Additionally, the selection is also guided by, for instance, whether the deprotected biotin will maintain substantially the same binding affinity in comparison to biotin which was never protected (e.g., if the deprotected form retains a structural remnant of the protection that results in a modified biotin molecule with decreased affinity with streptavidin). The result of this step leaves the unprotected biotin 100 with streptavidin 810 and R-phycoerythrin 820 unaffected, while providing an unprotected biotin 100 in place of previously protected biotin 540.

Step 4 within FIG. 8 illustrates the next step, which is the binding of a distinct avidin-label conjugate, such as streptavidin 810 conjugated with fluorescein 825. As depicted, the streptavidin 810 conjugated with R-phycoerythrin 820 remains unaffected, as only the biotin 100 which was deprotected within Step 3 is bound within Step 4 to the streptavidin 810 conjugated with fluorescein 825. Thus, this process facilitates two-color detection while employing only one binding interaction through the binding of biotin with streptavidin. This not only simplified the binding member interactions at issue within the assay, but also provides a simplified and more robust multi-color detection scheme that is not dependent on binding interactions that may involve inferior binding characteristics. For example, without the protection of biotin, a two-color assay would require a second binding pair, and this second binding pair is likely to impose upon the assay the issue of distinct binding characteristics. Additionally, many binding pairs will have inferior binding characteristics in comparison to biotin and streptavidin, and thus will have a relative lower affinity, a higher off-rate, poorer specificity, etc.

Figure 9:
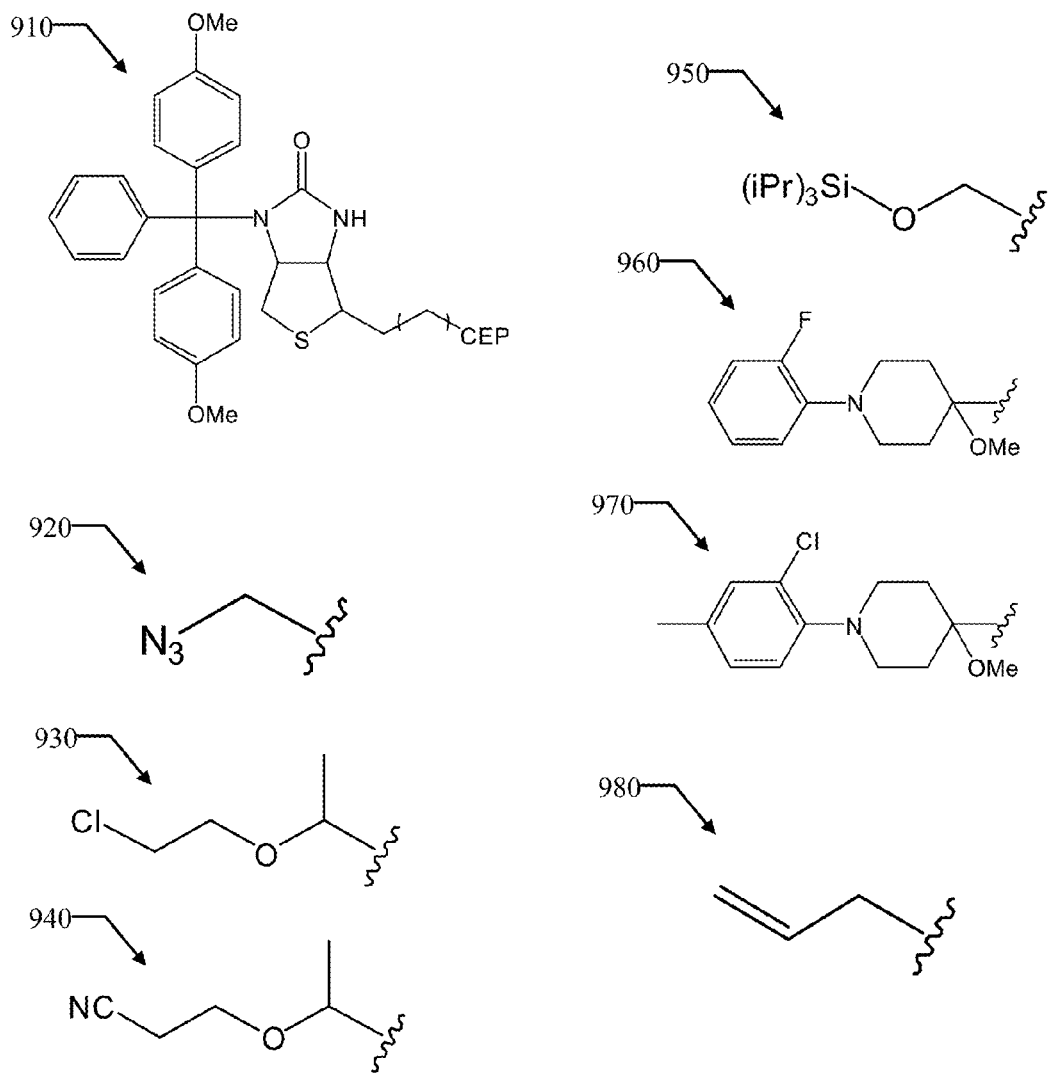
FIG. 9 illustrates non-limiting examples of alternative protecting groups.

While the above recited use of protected biotin included the use of biotin protected by NPOM, a photolabile protecting group, it should be recognized that other protecting groups, including non-photolabile protecting groups, may also be employed within certain embodiments. For example, within FIG. 9, an alternative version of the protected biotin depicted within FIG. 1(B) is illustrated, with protecting group 105 comprising dimethoxytrityl (DMT). Additional non-limiting examples of suitable protecting groups are also provided within FIG. 9, including azidomethyl (920), 1-(2-chloroethoxy)ethyl (CEE) (930), 1-(2-cyanoethoxy)ethyl (940), tri-isopropylsilyoxymethyl (TIPSOM) (950), 1-(2-fluorophenyl)-4-methoxypiperidin-4-yl (FPMP) (960), 1-(2-chloro-4-methylphenyl)-4-methoxypiperidin-4-yl (CTMP) (970) and allyl (980). Certain embodiments may employ protecting groups 105 which distinct removal conditions so as to facilitate their combined use within an assay. For example, azidomethyl, illustrated within FIG. 9 as structure 920, can be removed upon treatment of a phosphine based reagent (e.g., triphenylphosphine). Further examples of protecting groups which are suitable for certain embodiments include those described in "Protecting Groups," Phillip J. Kocieński, Thieme (3rd Ed. 2005); "Greene's Protecting Groups in Organic Synthesis," Peter G. M. Wuts and Theodora W. Greene, Wiley-Interscience (4th Ed. 2006); "Handbook of Synthetic Photochemistry," Angelo Albini and Maurizio Fagnoni (Eds.), Wiley-VCH (2010); U.S. Pat. No. 6,147,205 to McGall et al.; U.S. Pat. No. 7,547,775 to Kuimelis et al.; U.S. Patent Application Publication No. 2011/0028350; U.S. Patent Application Publication No. 2003/0040618 to McGall et al.; and U.S. Patent Application Publication No. 2006/0147969 to Kuimelis et al., all of which are incorporated herein by reference in their entireties for all purposes, and particularly for their disclosed protecting groups and related methods of manufacture and use. As stated earlier, selection of an appropriate protecting group 105 is based upon factors such as effective prevention of avidin binding to the protected biotin at issue, restoration of substantial binding affinity for the biotin after appropriate deprotection, compatibility with associated deprotection mechanisms with the assay (e.g., for the assay depicted in FIG. 9, a deprotection mechanism should not denature the hybridized nucleic acids through pH or salt changes), and other factors known in the art.

DMT is an exemplary non-limiting example of a protecting group that is not removed through photolysis, but instead through alternative means, such as treatment with an acid for DMT. Thus, alternative embodiments of the process illustrated within FIGS. 7(A)-7(D) and 8 utilize a non-photolabile protecting group, such as DMT, as protecting group 105 for the second set of labeled probes 635. Accordingly, Step 3 within FIG. 8 would be modified such that deprotection comprises an appropriate means for the non-photolabile protecting group on protected biotin 540. As a non-limiting example, if protected biotin 540 was protected by DMT, then Step 3 may comprise treatment with trichloroacetic acid to remove the DMT and free the biotin for binding with an appropriate avidin-label conjugate. Other suitable alternative acids may also be employed, such as trifluoroacetic acid, acetic acid or monopotassium phosphate. These and other suitable acids may be employed at pH values of, for example, 2.0, 2.5, 3.0, 3.5, or 4.0. This approach facilitates use of biotin and the two distinct avidin-label conjugates as described but without the need for appropriate illumination to deprotect the biotin by removal of, e.g., the NPOM protecting group. Such an non-photolabile alternative is helpful in certain embodiments, such as within those assays where the washing and staining steps are performed (either manually or in an automated fashion) without the ability to illuminate the protected biotin 540 with wavelength(s) appropriate to remove a photolabile protecting group, or within those assays where the particular wavelength(s) that would be employed to remove the protecting groups would damage or otherwise alter one or more components.

It should be noted that non-limiting example described above and depicted within FIGS. 7(A)-7(D) and 8 are merely a non-limiting example of a potential application of the labeling approach more broadly described herein and depicted within FIG. 6. Regardless of the particular labeling approach at issue, of which many are known in the art in addition to the ligation of labeled probes illustrated in FIGS. 7(A)-7(D) and 8, the basic principles discussed with respect to FIG. 6 will apply. Thus, it will be apparent to one of skill in the art to employ such a labeling approach to many other applications within the life sciences, such as other nucleic acid and protein array assays, nucleic acid sequencing, real time PCR, non-array based proteomics applications, antibody studies, various types of single cell analysis, and other applications known in the art where labels, including but not limited to fluorescent labels, are employed.

Biotin Derivatives

Many embodiments, including the previous embodiments described herein, may additionally employ biotin derivatives in place of traditional biotin. One such derivative employed in many embodiments is desthiobiotin, as was described earlier and illustrated within FIG. 4. The use of biotin derivatives, such as desthiobiotin, can be found in, e.g., Hirsch et al., "Easily reversible desthiobiotin binding to streptavidin, avidin, and other biotin-binding proteins: uses for protein labeling, detection, and isolation," Analytical Biochemistry, 308: 343-357 (2002), which is incorporated herein by reference in its entirety for all purposes. Desthiobiotin is useful with many embodiments described herein because biotin possesses a much stronger binding affinity with streptavidin ($1\times10^{15}$ $M^{-1}$ for biotin compared to $5\times10^{13}$ $M^{-1}$ for desthiobiotin) and because desthiobiotin can be displaced by a biotin solution. This usefulness is enhanced in view of the ability for biotin binding with appropriate biotin-binding proteins (e.g., avidin, streptavidin) to be essentially irreversible under common conditions for genomic or proteomic assays. For instance, most such assays are incompatible with common techniques to reverse any binding that has already occurred through the use of, e.g., extremely low pH values or high concentrations of chaotropic agents. Thus, within most assays, once a biotinylated target (e.g., a biotinylated nucleic acid, polypeptide, antibody) is bound with an appropriate protein (e.g., a streptavidin conjugated with a fluorophore), the binding and therefore labeling of that target is permanent for the purposes of the assay. This is one major contributing factor to the use of distinct binding pairs within assays, even though such use subjects the associated labeling process to dependency upon using a binding pair with different binding affinity values than say, streptavidin with biotin. Such use of other binding pairs can often lead to less desirable binding characteristics such as lower affinity, higher off-rate and lower specificity. Accordingly, these undesirable characteristics are passed onto the applicable labeling approach for those targets, and must be appropriately compensated for within subsequent detection and analysis.

Figure 10:
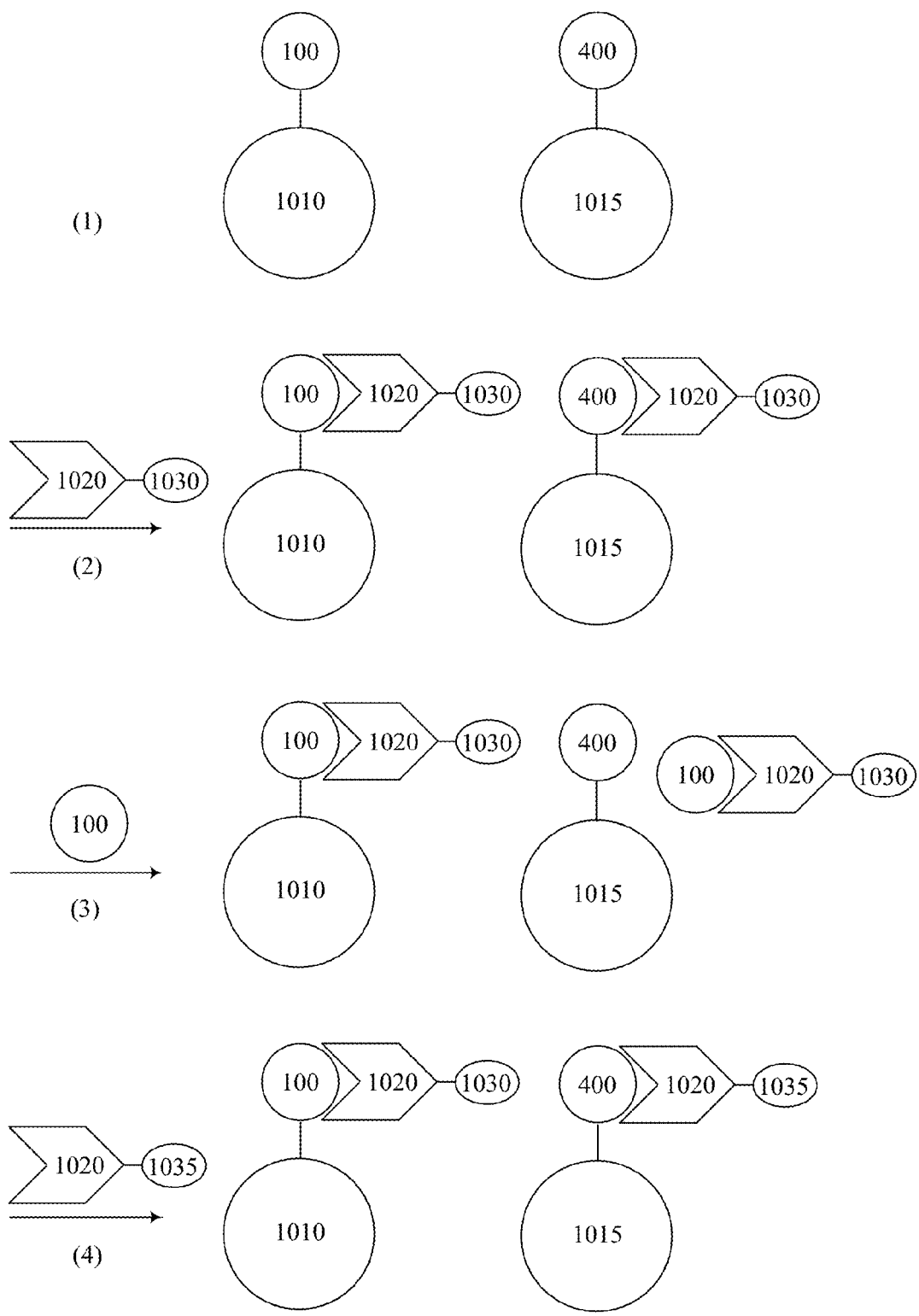
FIG. 10 illustrates a non-limiting example of a labeling scheme incorporating the use of biotin and desthiobiotin.

FIG. 10 depicts a non-limiting example of a general labeling scheme for the use of multiple types of labels through the use of biotin with desthiobiotin that can be employed in many different applications, as will be apparent to one of skill in the art upon reading the disclosure herein. Step 1 depicts the results of biotinylation (through any suitable means, including direct and indirect techniques) of a first target 1010 and a second target 1015. First and second targets 1010 and 1015 may be any suitable target, including nucleic acids, proteins, antibodies, cells (e.g., biotinylation of cell surface proteins), and any other suitable target known in the art. Specifically, first target 1010 is biotinylated with an unprotected biotin 100 while second target 1015 is biotinylated with a desthiobiotin 400.

Step 2 of FIG. 10 depicts the addition of an appropriate biotin binding protein 1020 which is conjugated with a first label 1030. Any suitable biotin binding protein can be employed, including natural, artificial, and modified proteins, which include but are not limited to avidin, streptavidin, recombinant versions thereof, ExtrAvidin® protein (Sigma-Aldrich Corporation, St. Louis, Mo.), NeutrAvidin® protein (Thermo Fisher Scientific, Inc., Waltham, Mass.), CaptAvidin™ protein (Life Technologies Corporation, Carlsbad, Calif.), and other suitable proteins known in the art. First label 1030 may be any suitable label as discussed herein and that is desired for the particular labeling scheme at issue, including the aforementioned non-limiting examples of fluorescent, luminescent, chemiluminescent, light-scattering, and colorimetric labels. As seen with Step 2 of FIG. 10, biotin binding protein 1020 binds with both the biotin 100 of first target 1010 and with the desthiobiotin 400 of second target 1015.

Step 3 of FIG. 10 depicts the displacement of the biotin binding protein 1020 conjugated with first label 1030 from only second target 1015. The displacement occurs through the addition of a biotin solution. As biotin has a significantly greater affinity for most biotin binding proteins, such as streptavidin, in comparison to desthiobiotin, the added biotin will essentially displace the desthiobiotin 400 with respect to the biotin binding protein 1020 which was previously bound to the desthiobiotin 400 of second target 1015. The exact manner of biotin displacement will vary depending on the particular embodiment, the assay conditions, and many other factors known in the art. For certain embodiments, use of a 1 mM solution of biotin is sufficient to displace desthiobiotin 400. However, for other embodiments, the concentration may need to be adjusted by a person of skill in the art to suit the specific requirements of the assay at issue. In most embodiments, Step 3 will also involve the washing, filtering or otherwise removal of the displaced biotin binding protein 1020 now bound to the newly added biotin 100.

Step 4 of FIG. 10 depicts the addition of biotin binding protein 1020, which is conjugated with a second label 1035. Second label 1035 is distinguishable from first label 1030 under the appropriate detection conditions (as required by the particular characteristics of first and second labels 1030 and 1035). Thus, second target 1015 is labeled with second label 1035 through the binding of the added protein conjugated label. This addition, however, does not affect the labeling of first target 1010 with the already bound conjugate of biotin binding protein 1020 and first label 1030. In many embodiments, the particular biotin binding protein 620 employed within Step 4 is the same type of protein utilized within Step 2. In this manner, the same relevant binding pair of biotin 100 and biotin binding protein 620 is employed for both first and second targets 610 and 615. However, the biotin binding protein 1020 conjugated with second label 1035 may be a different binding protein if so desired. While the binding affinities of the two binding pairs are different, the common use of biotin still provides the advantage of more similar binding characteristics of the two binding pairs in comparison to many other alternatives known in the art.

Furthermore, many variants of the process depicted within FIG. 10 will be apparent to one of skill in the art. For example, while the non-limiting example depicted within FIG. 10 employed desthiobiotin, the principles disclosed herein may be applied with respect to other suitable biotin analogues and derivatives. Selection of a suitable biotin analogue or derivative would be based upon factors such as its binding affinity for the biotin binding proteins at issue within the assay in relative comparison to biotin (and relative to any other biotin analogues or derivatives also employed within the assay). Appropriate selection of the biotin analogue(s) and/or derivative(s) allows selective displacement and re-labeling to enable multiple label use, including 2, 3, 4, 5, 6, 7, 8, 9, 10, and more labels to be employed.

Figure 11A:
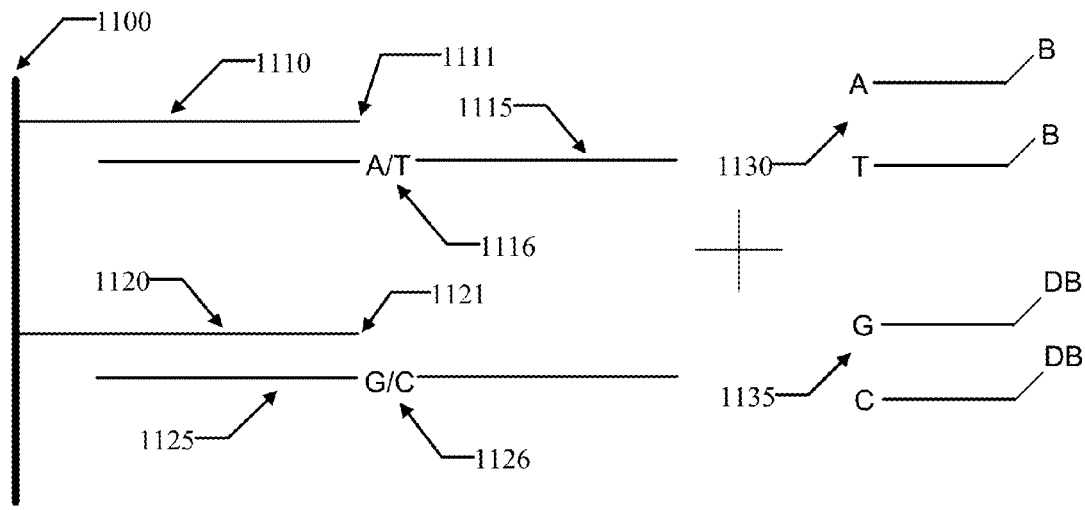
FIGS. 11(A)-11(B) illustrate a non-limiting example of a labeling scheme involving hybridized nucleic acids and ligation with a set of oligonucleotides which possess biotin or desthiobiotin to facilitate multiple label use.

Embodiments combining the use of desthiobiotin with biotin facilitate powerful multiple label approaches. FIGS. 11(A)-11(D) and 12 illustrate a non-limiting example of such use. The example depicted within those figures is a modification of the use and approach described within FIGS. 7(A)-7(D) and 8. Specifically, as shown in FIG. 11(A), support 1100 possesses a first oligonucleotide 1110 with a reactive end 1111 capable of ligation, and also a second oligonucleotide 1120 with a reactive end 1121 capable of ligation. As depicted within FIG. 11(A), first oligonucleotide 1110 has already been hybridized with target 1115 while second oligonucleotide 1120 has been hybridized with target 1125. The design of first oligonucleotide 1110 and second oligonucleotide 1120 is such that non-hybridized base 1116 and non-hybridized base 1126 are the first bases of targets 1115 and 1125 which are not hybridized with the oligonucleotides on the support. Furthermore, the design has been such that non-hybridized base 1116 is either an A or T while non-hybridized base 1126 is either a G or C.

Figure 11B:
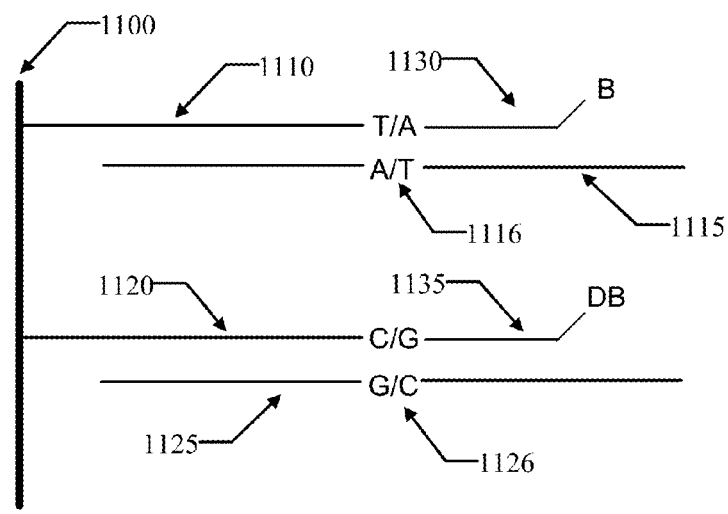
Figure 11C:
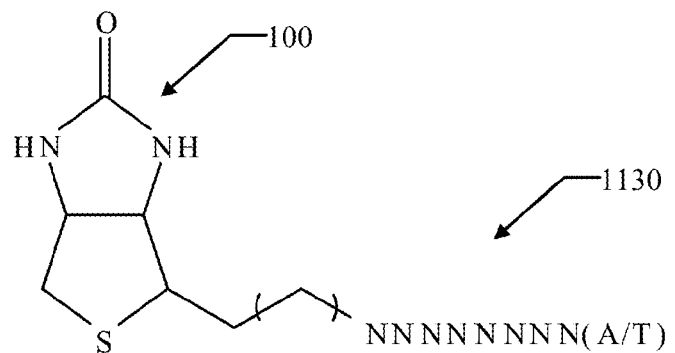
FIGS. 11(C)-11(D) illustrate non-limiting examples of the set of oligonucleotides with either biotin or desthiobiotin as used within the depiction of FIGS. 11(A)-11(B).
Figure 11D:
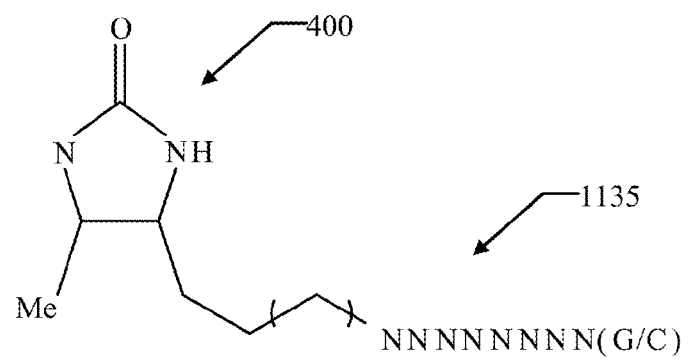

FIG. 11(A) also shows the addition of a first set of labeled probes 1130 and a second set of labeled probes 1135, which are illustrated in more detail within FIGS. 11(C) and 11(D) respectively. Specifically, FIG. 11(A) shows the first set of labeled probes 1130, which in this particular example possesses 8 universal bases and either an A or T to hybridize with non-hybridized base 1116, and where "B" represents biotin 100. As before and as described in association with FIGS. 7(A)-7(D) and 8, many alterations of this example are possible (e.g., changes to the number of universal bases). FIG. 11(D) depicts an example of a probe from the second set of labeled probes 1135, which also has 8 universal bases but instead possesses a G or C to hybridize with non-hybridized base 1126, and where "DB" represents desthiobiotin 400. Differences between the first set of labeled probes 1130 and second set of labeled probes 1135 with respect to the first set of labeled probes 630 and second set of labeled probes 635 is the absence of protecting groups for the biotin molecule and the substitution of desthiobiotin within the second set of labeled probes 1135. Thus, the result of appropriate ligation of the first and second sets of labeled probes 1130 and 1135 is shown in FIG. 11(B), with first oligonucleotide 1110 ligated to an appropriate probe of the first set of labeled probes 1130, based on the exact identity of non-hybridized base 1116, and second oligonucleotide 1120 is ligated to an appropriate probe of the second set of labeled probes 1135, based on the exact identity of non-hybridized base 1126.

Figure 12:
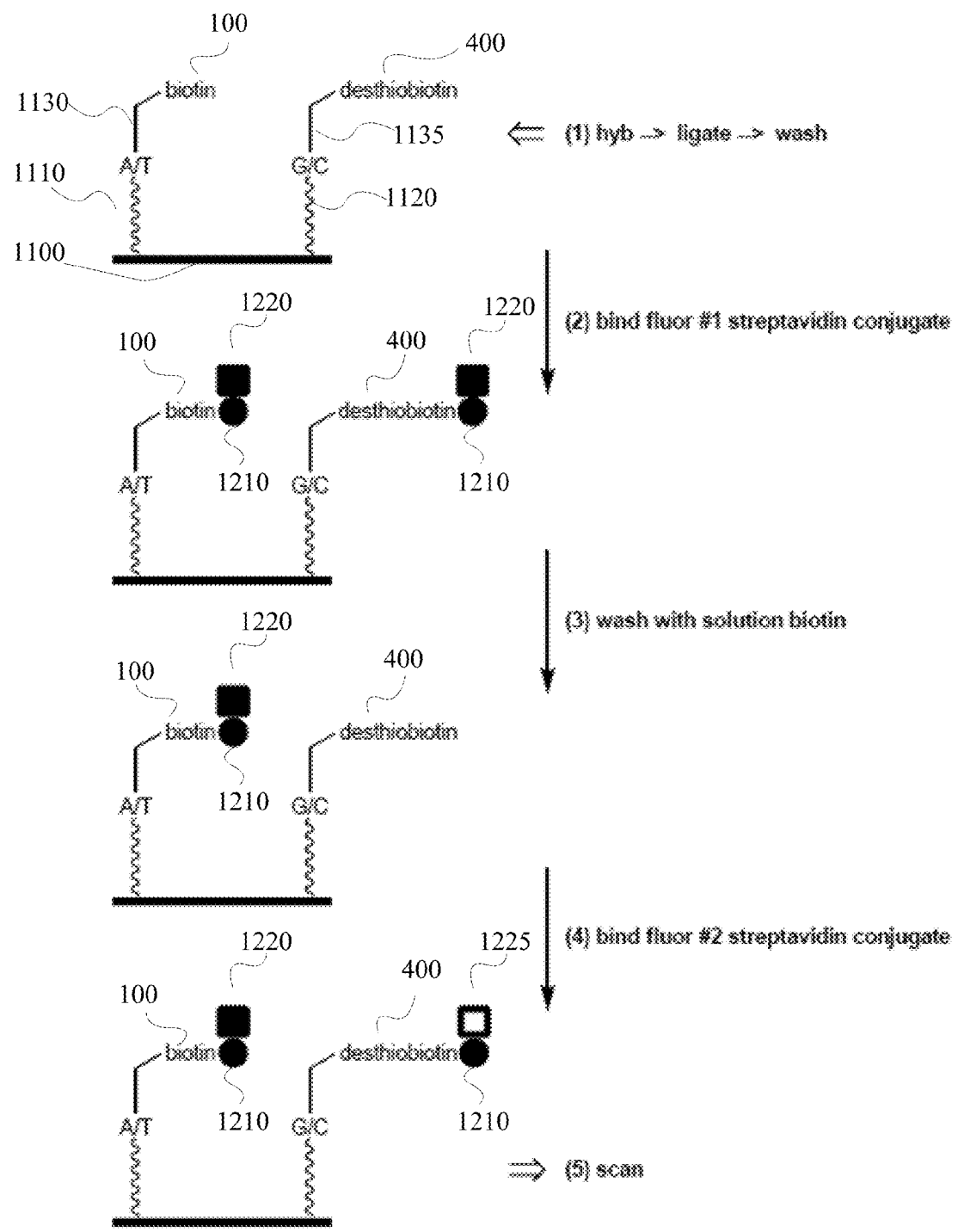
FIG. 12 illustrates a non-limiting example of selectively employing two labels within the example depicted within FIGS. 11(A)-11(D).

The illustration of this particular non-limiting example of utilizing biotin and desthiobiotin within an assay is continued within FIG. 12. Specifically, Step 1 within FIG. 12 depicts the results from FIG. 11(B), with first oligonucleotide 1110 ligated to a probe of the first set of labeled probes 1130 and second oligonucleotide 1120 ligated to a probe of the second set of labeled probes 1135. As depicted in FIGS. 11(A)-11(D), probes from the first set of labeled probes 1130 possess an unprotected biotin 100 while probes from the second set of labeled probes 1135 possess desthiobiotin 400. For ease of reference within FIG. 12, targets 1115 and 1125 are not expressly shown, but are, in this particular non-limiting example, still hybridized with the first and second oligonucleotides 1110 and 1120 and probes from the first and second sets of labeled probes 1130 and 1135.

Step 2 within FIG. 12 depicts the results of binding an avidin-conjugate, such as streptavidin 1210 conjugated with a first label 1220. In this particular non-limiting example, the first label 1220 is a fluorophore, but alternative embodiments employ other labels, including non-fluorescent labels. Step 2 depicts the ability of many biotin binding proteins (e.g., avidin, streptavidin) to bind to both biotin and biotin derivatives (e.g., the desthiobiotin employed here), as streptavidin 1210 binds to both biotin 100 and desthiobiotin 400.

Step 3 within FIG. 10 show the next step within the assay, which involves washing with a biotin solution. The biotin within the solution displaces the desthiobiotin previously bound to streptavidin 1210 conjugated with the first label 1020. The free biotin-streptavidin 1210—first label 1220 complex can then be washed away from support 1100.

Step 4 within FIG. 10 depicts the next step, where streptavidin 1210, which is conjugated to a second label 1225 (which is illustrated here as a different fluorescent label than first label 1220, but which can be any suitable label, including non-fluorescent labels), is bound to the desthiobiotin 400 of the second set of labeled probes 1135.

It should be noted that non-limiting example described above and depicted within FIGS. 11(A)-11(D) and 12 are merely a non-limiting example of a potential application of the labeling approach more broadly described herein and depicted within FIG. 10. Regardless of the particular labeling approach at issue, of which many are known in the art in addition to the ligation of labeled probes illustrated in FIGS. 11(A)-11(D) and 12, the basic principles discussed with respect to FIG. 10 will apply. Thus, it will be apparent to one of skill in the art to employ such a labeling approach to many other applications within the life sciences, such as other nucleic acid and protein array assays, nucleic acid sequencing, real time PCR, non-array based proteomics applications, antibody studies, various types of single cell analysis, and other applications known in the art where labels, including but not limited to fluorescent labels, are employed.

Multiple Label Use Combining Biotin, Desthiobiotin, and Protected Biotin

As described herein, protected biotin can be employed with unprotected biotin to facilitate multiple label approaches (including those utilizing 2, 3, 4, 5, 6, 7, 8, 9, 10 or more distinct types of labels), where the relevant binding pair (e.g., biotin and streptavidin) is the same to facilitate a more effective and easily analyzed assay that provides superior labeling abilities in comparison to multiple label approaches which possess different binding pairs for the labels. Also described herein are approaches where biotin is employed with desthiobiotin to provide an alternative avenue for multiple label approaches which take advantage of the ability of biotin to displace desthiobiotin in its binding with appropriate biotin binding proteins (e.g., avidin, streptavidin). However, these approaches can also be combined to easily facilitate 4 or more label assays which continue to employ the biotin (and relevant biotin analogues and derivatives) binding relationship with relevant biotin binding proteins. For example, the approaches described within FIGS. 6 and 10, directed toward the use of protected biotin with unprotected biotin and toward the use of biotin with desthiobiotin, respectively, can additionally be combined within a labeling scheme. In this manner, four distinct biotinylated targets can be labeled appropriately with one of four labels.

For example, in a combination and expansion of the approaches described herein with respect to FIGS. 6 and 10, four different targets of interest can be biotinylated with biotin, desthiobiotin, biotin protected by a first protecting group, and biotin protected by a second protecting group, respectively. Then, through the approaches described herein of adding appropriately labeled biotin binding proteins conjugated with a label (or labels), each of the four targets can be appropriately labeled after deprotection of the protecting group, biotin washing and displacement of biotin binding proteins bound to the desthiobiotin, etc. The same concerns will also be relevant in such an application that is expanded to four (or more labels). For example, with the use of two or more (e.g., 2, 3, 4, 5, 6, 7, 8, 9, 1) protecting groups within such embodiments, the protecting groups must be chosen in a manner such that the associated deprotection mechanisms will not remove other protecting groups in addition to the ones desirably removed within a specific assay step. For example, within a four color approach utilizing two different protecting groups, a non-limiting example may employ DMT to be removed with a trifluoroacetic acid treatment and azidomethyl to be removed with a phosphine based treatment.

III. EXAMPLES

Example 1

A Two-Color Coding Method Using DMT Protected Biotin

An experiment was performed according to the scheme illustrated within FIGS. 7(A)-7(D) and 8 to demonstrate a two-color system which utilizes unprotected biotin in combination with DMT protected biotin. A DNA probe array containing a DNA probe array containing 5'-phosphorylated 35mer probes was fabricated using conventional photolithographic techniques. Two synthetic 50mer DNA targets (10 nM in high-salt buffer) were contacted with the array for 24 hours at 45° C., with subsequent removal of non-hybridized target via washing with a reduced salt concentration buffer for 30 minutes at 37° C. The resulting array was then contacted with a mixture containing 5'-B-N8-A/T (50 uM), 5'-PB-N-8-G/C (50 uM), E. Coli DNA ligase (USB Corporation, Cleveland, Ohio) and E. Coli ligase buffer (New England Biolabs, Inc., NEB, Ipswich, Mass.) for a period of 3 hours at room temperature. PB is DMT protected biotin, B is unprotected biotin, N represents degenerate universal bases and A/T or G/C represents a 1:1 ratio of the indicated two bases within the respective probe set mixtures. Non-ligated components were subsequently removed by washing the array with low-salt TE buffer at 50° C. Thus, the initially available biotinylated probes that were not protected from streptavidin binding were the ones with the A or T as the $9^{th}$ base of the probe, and which were ligated to the 5' end of the 35mer probes. These probes were then stained with streptavidin-phycoerythrin conjugate by contacting the array with stain solution for 5-10 minutes before excess reagents were removed. The next step was to deprotect the biotin of the ligated G/C probes. The array was treated with a citrate buffer (30 mM, pH 3.5) in NaCl (150 mM) for 30 minutes at room temperature before excess reagents were removed. The newly available biotinylated probes (i.e., the probes whose biotin was now deprotected) were stained by contacting the array with streptavidin-phycoerythrin-Cy5 conjugate, followed by removal of excess reagents.

Array fluorescence imaging in two separate channels with the wavelengths appropriate for the two fluorophores reveals the ability of the protected biotin to resist the first biotin-specific stain, yet become available for a subsequent biotin-specific stain step after the biotin protecting group (DMT) was removed with, in this particular example, a mild acid treatment. The signal obtained from the fluorescent emissions associated with the streptavidin-phycoerythrin conjugate bound to the ligated 9mers with an A or T produced a signal-to-background ratio of 25.9. Meanwhile, the signal obtained from the fluorescent emissions associated with the streptavidin-phycoerythrin-Cy5 conjugate bound to the ligated 9mers with a G or C produced a signal-to-background ratio of 6.0. Even higher ratios can be obtained with appropriate selection of the utilized fluorophores.

Figure 13A:
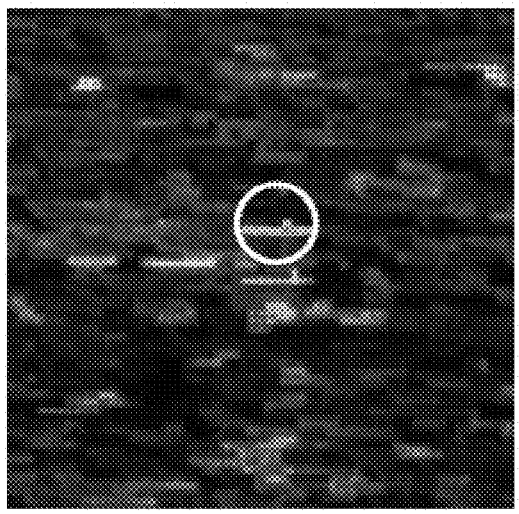
FIGS. 13(A)-13(B) contain images of arrays utilized to measure the ability of a DMT protecting group to prevent a streptavidin fluorophore conjugate from binding with the protected biotin.
Figure 13B:
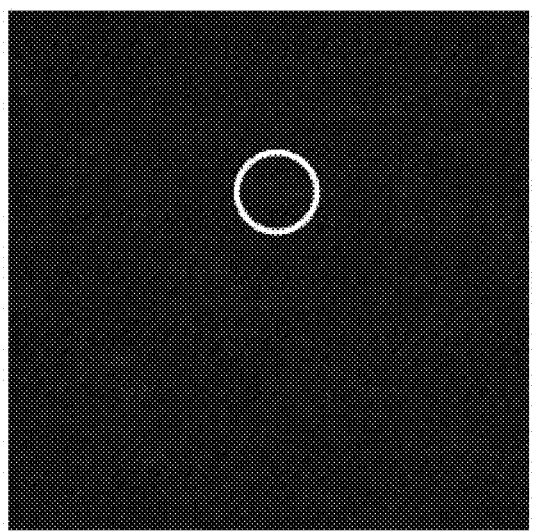

FIGS. 13(A)-13(B) contain images of sub-regions of an array prepared as described above as a demonstration of stability for DMT protected biotin during a ligation reaction period of 3 hours. The encircled region within FIG. 13(A) surrounds a set of probes relevant to the synthetic target 45mer recited above. As can be seen from a sampling of specific intensity values within FIG. 13(A) for various positions of the sets of probes, the intensity for unprotected biotin that is stained with SAPE is extremely strong. Conversely, within FIG. 13(B), which has an encircled region surrounding sets of probes ligated with DMT protected biotin after identical SAPE staining, the sampling of specific intensity values demonstrates that DMT retains its effectiveness in protecting biotin from binding with SAPE even after exposure to extended ligation reactions if the appropriate acid treatment is not performed to remove the DMT.

Figure 14A:
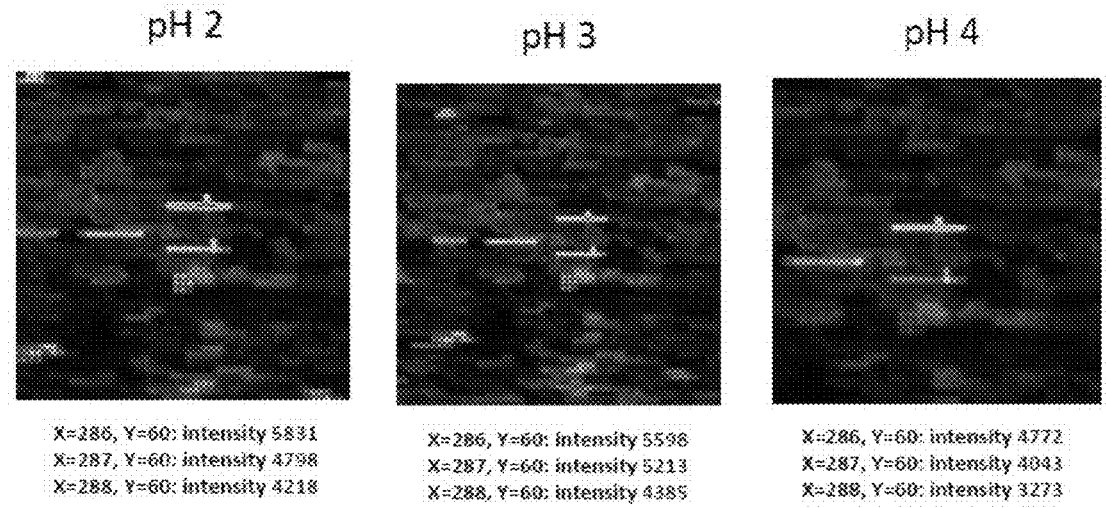
FIGS. 14(A)-14(C) contain images of arrays utilized to measure the ability of selected acids at different pH values to remove DMT protecting groups from biotin and allow desired binding with a streptavidin fluorophore conjugate.
Figure 14B:
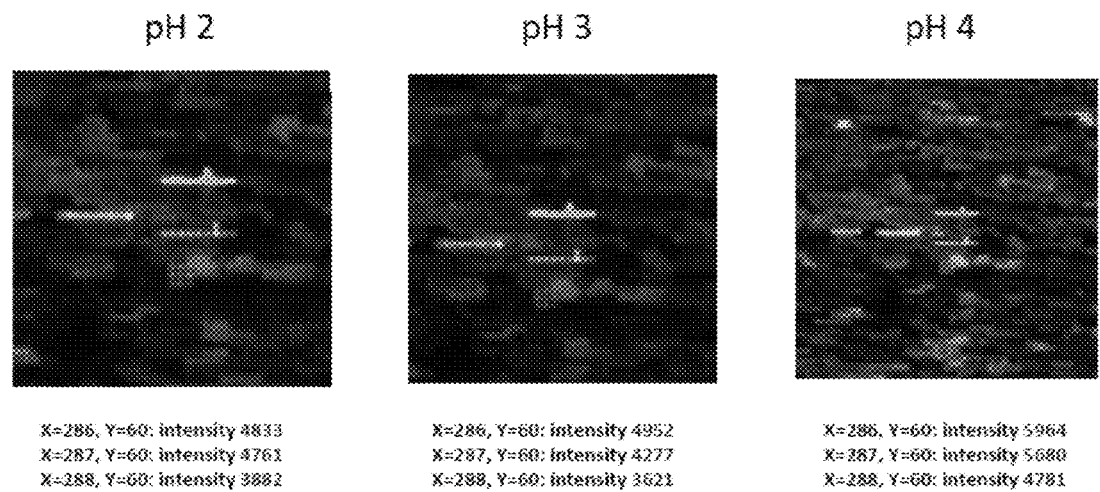
Figure 14C:
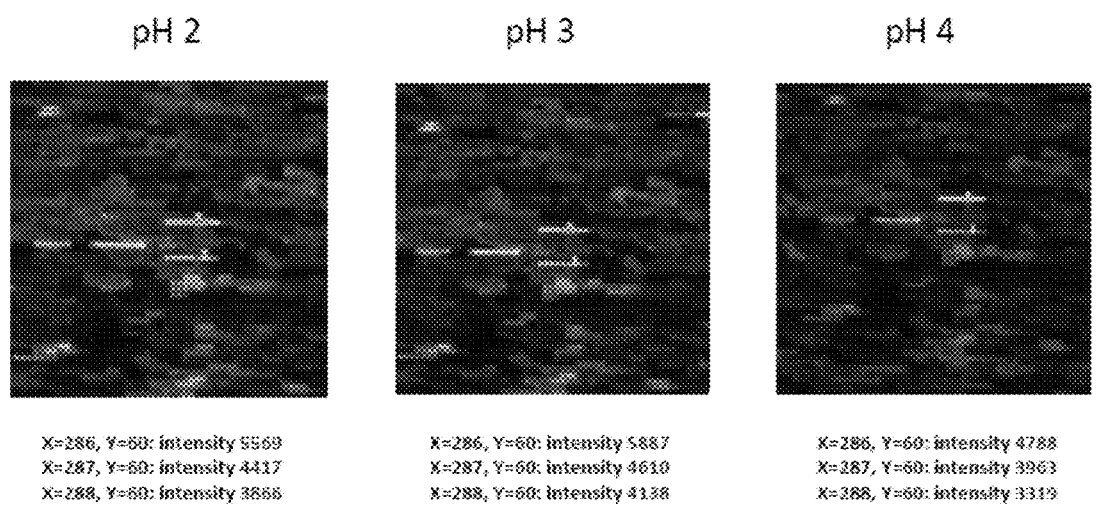

FIGS. 14(A)-14(C) contains demonstrations of the flexibility of DMT protection for biotin. Specifically, the images within FIG. 14(A) display arrays which underwent detritylation of the DMT protected biotin with trifluoroacetic acid solutions with pH values of 2, 3 and 4 for 30 minutes before staining as described above. FIG. 14(B) contains images corresponding to arrays where the detritylation of DMT protected biotin occurred via acetic acid solutions with pH values of 2, 3 and 4 for 30 minutes before staining FIG. 14(C) contains images corresponding to arrays where the DMT protected biotin was remove through 20 mM $KH_2PO_4$ for 30 minutes before staining. The ability of utilizing different deprotection mechanisms provides flexibility benefits within many assays, especially those employing orthogonal protection schemes as appropriate selection of deprotection mechanisms can enhance the effectiveness and efficiency of utilizing multiple types of biotin protecting groups to enable additional color capabilities within multi-color labeling schemes.

Example 2

A Two-Color Coding Method Using Biotin and Desthiobiotin

An experiment was performed according to the scheme illustrated within FIGS. 11(A)-11(D) and 12 to demonstrate a two-color system which utilizes unprotected biotin in combination with desthiobiotin. A DNA probe array containing a DNA probe array containing 5'-phosphorylated 35mer probes was fabricated using conventional photolithographic techniques. Two synthetic 50mer DNA targets (10 nM in high-salt buffer) were contacted with the array for 24 hours at 45° C., with subsequent removal of non-hybridized target via washing with a reduced salt concentration buffer for 30 minutes at 37° C. The resulting array was then contacted with a mixture containing 5'-DB-N8-A/T (50 uM), 5'-B-N8-G/C (50 uM), E. Coli DNA ligase (USB Corporation, Cleveland, Ohio) and E. Coli ligase buffer (New England Biolabs, Inc., NEB, Ipswich, Mass.) for a period of 3 hours at room temperature. DB is desthiobiotin, B is unprotected biotin, N represents degenerate universal bases and A/T or G/C represents a 1:1 ratio of the indicated two bases within the respective probe set mixtures. Non-ligated components were subsequently removed by washing the array with low-salt TE buffer at 50° C. Thus, the initially available biotinylated probes that were both the ones with the A or T as the $9^{th}$ base of the probe and which contained desthiobiotin, and also those probes with the G or C as the $9^{th}$ base of the probe and which contained biotin. All ligated probes were then stained with streptavidin-phycoerythrin conjugate by contacting the array with stain solution for 5-10 minutes before excess reagents were removed. The next step was to displace the streptavidin-phycoerythrin conjugate bound to the desthiobiotin of the ligated A/T probes. This was done by washing the array with solution biotin (1 mM) in NaCl (150 mM) for 4 hours at room temperature. The displaced streptavidin-phycoerythrin conjugate previous bound to the desthiobiotinylated probes was then removed. The newly available desthiobiotinylated were then stained by contacting the array with streptavidin-phycoerythrin-Cy5 conjugate, followed by removal of excess reagents.

Array fluorescence imaging in two separate channels with the wavelengths appropriate for the two fluorophores reveals the ability of the unprotected biotin to retain the first stain of streptavidin-phycoerythrin, and also the ability of the desthiobiotin to be displaced by a biotin solution and readily bind to the second stain of streptavidin-phycoerythrin-Cy5 conjugate. The signal obtained from the fluorescent emissions associated with the streptavidin-phycoerythrin conjugate bound to the ligated 9mers with an A or T produced a signal-to-background ratio of 12.5. Meanwhile, the signal obtained from the fluorescent emissions associated with the streptavidin-phycoerythrin-Cy5 conjugate bound to the ligated 9mers with a G or C produced a signal-to-background ratio of 2.3. Even higher ratios can be obtained with appropriate selection of the utilized fluorophores.

Figure 15A:
FIGS. 15(A)-15(C) contain images of arrays utilized to measure the ability of desthiobiotin to bind with a streptavidin fluorophore conjugate, have the streptavidin fluorophore conjugate be displaced by a biotin solution, and rebind with a streptavidin fluorophore conjugate.
Figure 15B:
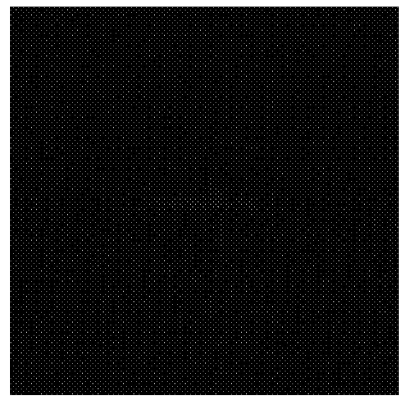
Figure 15C:
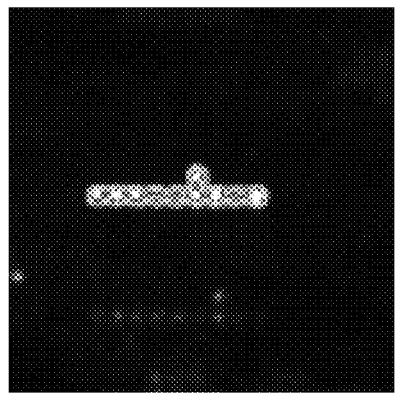

FIGS. 15(A)-15(C) contain images of sub-regions with sets of probes to test the effectiveness of binding and displacement of desthiobiotin with biotin. Specifically, the probe sets within the images are ligated with desthiobiotin labeled probes. The image within FIG. 15(A) shows probes which have been stained with streptavidin phycoerythrin. The image within FIG. 15(B) shows the probes after treatment with a 1 mM biotin solution to displace the desthiobiotin from the SAPE. Washing was also performed to remove the displaced biotin-SAPE conjugate. FIG. 15(C) contains an image after subsequent restraining with SAPE. These figures demonstrate the ability effectively displace and remove a labeling stain from desthiobiotin, and to effectively re-stain desthiobiotin with a second biotin binding protein-label conjugate after displacement of the first biotin binding protein-label conjugate.

It is to be understood that the above description, including any examples provided herein, is intended to be illustrative and not restrictive. Many variations of the invention will be apparent to those of skill in the art upon reviewing the above description. The scope of the invention should be determined with reference to the appended claims, along with the full scope of equivalents to which such claims are entitled. All cited references, including patent and non-patent literature, are incorporated herein by reference in their entirety for all purposes.

What is claimed is:

1. A method of labeling a plurality of targets with a plurality of labels, the method comprising:
   providing a plurality of targets, wherein the plurality of targets comprises a first target and a second target, wherein the first target includes a first biotin molecule, and wherein the second target includes a second biotin molecule that is protected by a protecting group;
   binding the first biotin molecule with a first biotin binding protein, wherein the first biotin binding protein includes a first label;
   deprotecting the second biotin molecule, and
   binding the deprotected second biotin molecule with a second biotin binding protein, wherein the second biotin binding protein includes a second label, and wherein the first label is distinguishable from the second label.

2. The method of claim 1, wherein the plurality of targets was biotinylated to incorporate the first biotin molecule and the second biotin molecule.

3. A method of labeling a plurality of targets with a plurality of labels, the method comprising:
   providing a plurality of targets, wherein the plurality of targets comprises a first target and a second target, wherein the first target includes a first biotin molecule, and wherein the second target includes a second biotin molecule, wherein the first biotin molecule has a stronger binding affinity for a biotin binding protein compared to the second biotin molecule;
   binding the first biotin molecule and the second biotin molecule with a first biotin binding protein, wherein the first biotin binding protein includes a first label;
   removing the first biotin binding protein from the second biotin molecule by introduction of a solution of the first biotin molecule, and
   binding the second biotin molecule with a second biotin binding protein including a second label, and wherein the first label is different from the second label.

4. The method of claim 3, wherein the first biotin molecule comprises biotin and the second biotin molecule comprises desthiobiotin.

5. The method of claim 1, wherein at least one of either the first biotin binding protein or the second biotin binding protein is streptavidin.

6. The method of claim 1, wherein at least one of either the first biotin binding protein or the second biotin binding protein is a recombinant protein.

7. The method of claim 1, wherein the first biotin binding protein is a different protein than the second biotin binding protein.

8. The method of claim 1, wherein the first label and the second label are fluorophores, wherein the first label has a first emission spectrum, wherein the second label has a second emission spectrum, and wherein the first emission spectrum is at least partially non-overlapping with the second emission spectrum.

9. The method of claim 1, wherein the protecting group is connected to the second biotin molecule through an ether linkage.

10. The method of claim 9, wherein the protecting group is 6-nitropiperonyloxymethyl.

11. The method of claim 1, wherein the protecting group is dimethoxytrityl.

12. The method of claim 4, wherein the plurality of targets additionally comprises a third target and a fourth target, wherein the third target includes a third biotin molecule protected by a first protecting group, wherein the fourth target includes a fourth biotin molecule protected by a second protecting group, and wherein the first protecting group and the second protecting group are different protecting groups.

13. The method of claim 12, additionally comprising:
   binding the third biotin molecule with a third biotin binding protein, wherein the third biotin binding protein includes a third label, and wherein the first protecting group is removed to allow the third biotin molecule to bind with the third biotin binding protein; and
   binding the fourth biotin molecule with a fourth biotin binding protein, wherein the fourth biotin binding protein includes a fourth label, and wherein the second protecting group is removed to allow the fourth biotin molecule to bind with the fourth biotin binding protein.

14. The method of claim 12, wherein the first biotin molecule is protected by a third protecting group, and wherein the second biotin molecule is protected by a fourth protecting group.

15. The method of claim 13, wherein the first protecting group and the second protecting group are each removed through a distinct removal mechanism.

* * * * *